(12) United States Patent
Reed et al.

(10) Patent No.: US 6,410,507 B1
(45) Date of Patent: Jun. 25, 2002

(54) COMPOUNDS FOR IMMUNOTHERAPY AND DIAGNOSIS OF BREAST CANCER AND METHODS FOR THEIR USE

(75) Inventors: Steven G. Reed, Bellevue; Jiangchun Xu, Seattle; Davin C. Dillon, Redmond, all of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/346,327

(22) Filed: Jul. 2, 1999

Related U.S. Application Data

(63) Continuation-in-part of application No. 09/288,950, filed on Apr. 9, 1999, now abandoned, which is a continuation-in-part of application No. 09/248,178, filed on Feb. 9, 1999, which is a continuation-in-part of application No. 09/118,627, filed on Jul. 17, 1998, which is a continuation-in-part of application No. 08/998,253, filed on Dec. 24, 1997, now abandoned.

(51) Int. Cl.[7] .................. A61K 38/18; A61K 38/19; C07K 14/475; C07K 14/52

(52) U.S. Cl. .................. 514/2; 514/12; 530/350; 530/351; 530/399

(58) Field of Search .............. 435/7.92, 7; 424/184.1; 436/811, 814; 530/350, 351, 399; 514/2, 12

(56) References Cited

U.S. PATENT DOCUMENTS 5,015,571 A * 5/1991 Niman et al. .............. 435/7.92

FOREIGN PATENT DOCUMENTS

| EP | 0679716 A | 11/1995 |
|---|---|---|
| WO | WO 94/21287 | 9/1994 |
| WO | WO 94/23728 | 10/1994 |
| WO | WO 95/11986 | 5/1995 |
| WO | WO 95/19783 | 7/1995 |
| WO | WO 97/02280 | 1/1997 |
| WO | WO 97/25426 | 7/1997 |
| WO | WO 97/34921 | 9/1997 |
| WO | WO 98/18945 | 5/1998 |
| WO | WO 99/33869 | 7/1999 |

OTHER PUBLICATIONS

Fuhlendorff J et al, "Primary structure of tetranectin, a plasminogen kringle 4 binding plasma protein: homology with asialoglycoprotein receptors and cartilage proteoglycan core protein", Biochemistry 26:6757–6764 (1987).*
Hillier L et al, WashU–Merck EST Project 1997, Aug. 6, 1997, Accession No. AA242765.*
Welling et al., Choice of peptide and peptide length for the generation of antibodies reactive with the intact protein, FEBS 2315; vol. 182, No. 1, pp 81–84.*
Hillier et al. (AA399390, EST Database Record, Aug. 12, 1997).*
Neame et al., Primary structure of a protein isolated from reef shark (*Carcharhinus springeri*) cartilage that is similar to the mammalian C–type lectin homolog, tetranectin: Protein Science (1992), 1, 161–168. Cambridge University Press.*
Genbank Sequence Database, Accession No. AA124124, Feb. 17, 1997.
Genbank Sequence Database, Accession No. AA133706, Jul. 31, 1997.
Genbank Sequence Database, Accession No. AA150963, May 19, 1997.
Genbank Sequence Database, Accession No. AA163045, Feb. 16, 1997.
Genbank Sequence Database, Accession No. AA214632, Aug. 13, 1997.
Genbank Sequence Database, Accession No. AA243535, Aug. 15, 1997.
Genbank Sequence Database, Accession No. AA256631, Aug. 6, 1997.
Genbank Sequence Database, Accession No. AA258236, Aug. 13, 1997.
Genbank Sequence Database, Accession No. AA259166, Aug. 15, 1997.
Genbank Sequence Database, Accession No. AA299443, Apr. 18, 1997.
Genbank Sequence Database, Accession No. AA340069, Apr. 21, 1997.
Genbank Sequence Database, Accession No. AA364013, Apr. 21, 1997.
Genbank Sequence Database, Accession No. AA366358, Apr. 21, 1997.
Genbank Sequence Database, Accession No. AA413174, May 2, 1997.
Genbank Sequence Database, Accession No. AA425487, Oct. 16, 1997.
Genbank Sequence Database, Accession No. AA451680, Jun. 5, 1997.
Genbank Sequence Database, Accession No. AA456968, Jun. 6, 1997.
Genbank Sequence Database, Accession No. AA457077, Jun. 6, 1997.
Genbank Sequence Database, Accession No. AA478500, Aug. 8, 1997.
Genbank Sequence Database, Accession No. AA490863, Aug. 15, 1997.

(List continued on next page.)

*Primary Examiner*—Marianne P. Allen
(74) *Attorney, Agent, or Firm*—Seed Intellectual Property Law Group

(57) ABSTRACT

Compounds and methods for the treatment and diagnosis of breast cancer are provided. The inventive compounds include polypeptides containing at least a portion of a breast tumor protein. Vaccines and pharmaceutical compositions for immunotherapy of breast cancer comprising such polypeptides, or polynucleotides encoding such polypeptides, are also provided, together with polynucleotides for preparing the inventive polypeptides.

9 Claims, 1 Drawing Sheet

OTHER PUBLICATIONS

Figure 1A:
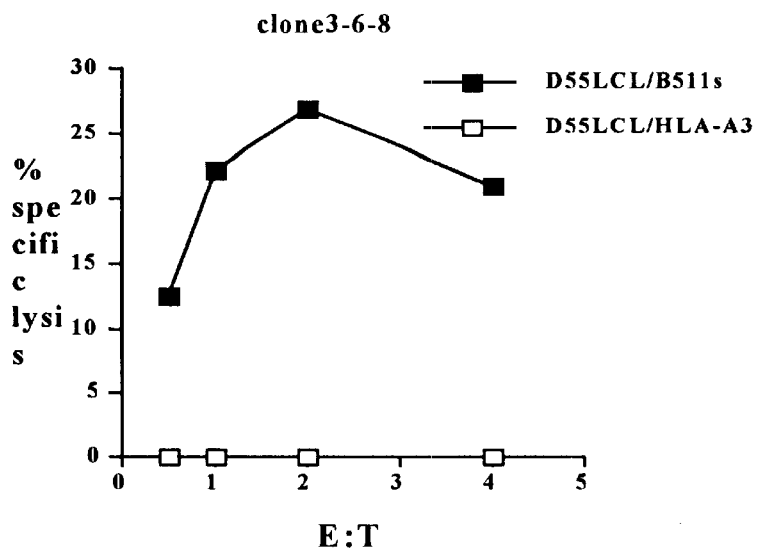

Genbank Sequence Database, Accession No. AA535894, Aug. 21, 1997.
Genbank Sequence Database, Accession No. AA535981, Aug. 21, 1997.
Genbank Sequence Database, Accession No. AA552419, Sep. 5, 1997.
Genbank Sequence Database, Accession No. AA610465, Oct. 30, 1997.
Genbank Sequence Database, Accession No. AA613497, Oct. 30, 1997.
Genbank Sequence Database, Accession No. AA626243, Oct. 15, 1997.
Genbank Sequence Database, Accession No. AA646568, Oct. 28, 1997.
Genbank Sequence Database, Accession No. AA701126, Dec. 19, 1997.
Genbank Sequence Database, Accession No. AA703778, Dec. 24, 1997.
Genbank Sequence Database, Accession No. AA722353, Jan. 2, 1998.
Genbank Sequence Database, Accession No. AA746345, Jan. 27, 1998.
Genbank Sequence Database, Accession No. AA775552, Feb. 5, 1998.
Genbank Sequence Database, Accession No. AA848022, Mar. 31, 1998.
Genbank Sequence Database, Accession No. AA856775, Jun. 9, 1998.
Genbank Sequence Database, Accession No. AA857943, Apr. 29, 1998.
Genbank Sequence Database, Accession No. AA962009, May 15, 1998.
Genbank Sequence Database, Accession No. AA971201, May 20, 1998.
Genbank Sequence Database, Accession No. AJ005890, May 15, 1998.
Genbank Sequence Database, Accession No. D50995, Sep. 14, 1995.
Genbank Sequence Database, Accession No. D59275, Aug. 28, 1995.
Genbank Sequence Database, Accession No. D80022, Feb. 9, 1996.
Genbank Sequence Database, Accession No. H21976, Jul. 6, 1995.
Genbank Sequence Database, Accession No. H21977, Jul. 6, 1995.
Genbank Sequence Database, Accession No. H25577, Jul. 10, 1995.
Genbank Sequence Database, Accession No. H25624, Jul. 10, 1995.
Genbank Sequence Database, Accession No. N48289, Feb. 14, 1996.
Genbank Sequence Database, Accession No. N49017, Feb. 14, 1996.
Genbank Sequence Database, Accession No. N54784, Jan. 28, 1997.
Genbank Sequence Database, Accession No. N59253, Feb. 23, 1996.
Genbank Sequence Database, Accession No. N62351, Mar. 1, 1996.
Genbank Sequence Database, Accession No. N76721, Apr. 2, 1996.
Genbank Sequence Database, Accession No. R75793, Jun. 6, 1995.
Genbank Sequence Database, Accession No. R78938, Jun. 9, 1995.
Genbank Sequence Database, Accession No. T21968, Aug. 5, 1996.
Genbank Sequence Database, Accession No. W02878, Apr. 18, 1996.
Genbank Sequence Database, Accession No. W72837, Oct. 16, 1996.
Genbank Sequence Database, Accession No. W72838, Oct. 16, 1996.
Genbank Sequence Database, Accession No. Z98046, Jul. 13, 1998.
Liang et al., "Differential Display and Cloning of Messenger RNAS from Human Breast Cancer Versus Mammary Epithelial Cell," *Cancer Research* 52:6966–6968, 1992.
Porter Jordan and Lippman, "Overview of the Biological Markers of Breast Cancer," *Breast Cancer* 8:73–100, 1994.
Schlom et al., "Strategies for the Development of Recominant Vaccines for the Immunotherapy of Breast Cancer," *Breast Cancer Research and Treatment* 38(1):27–39, 1996.
Watson and Fleming, "Isolation of Differentially Expressed Sequence Tags from Human Breast Cancer," *Cancer Research* 54(17):4598–4602, 1994.
Yee et al., "Isolation of Tyrosinase–Specific CD8$^+$ and CD4$^+$ T Cell Clones from the Peripheral Blood of Melanoma Patients Following In Vitro Stimulation with Recombinant Vaccinia Virus," *J. of Immunology* 157:4079–4086, 1996.
GenBank Accession No. AA749298, "Homo sapiens cDNA clone Image:1271152 3', mRNA sequence," Jan. 20, 1998.

* cited by examiner

Figure 1B:
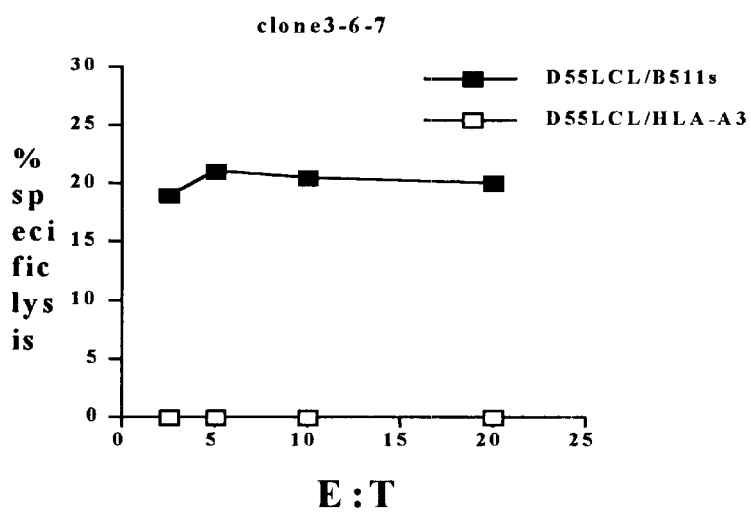

Figure 1: Specific lytic activity of B511s-specific CTL clones 3-6-8 and 3-6-7 measured on autologous LCL transduced with B511s (filled squares) or HLA-A3 (open squares). Each data point is the average of triplicate measurements.

COMPOUNDS FOR IMMUNOTHERAPY AND DIAGNOSIS OF BREAST CANCER AND METHODS FOR THEIR USE

REFERENCE TO RELATED APPLICATIONS

This application is, a continuation-in-part of U.S. patent application Ser. No. 09/288,950, filed Apr. 9, 1999, now abandoned, which is a continuation-in-part of U.S. patent application Ser. No. 09/248,178, filed Feb. 9, 1999, which is a continuation-in-part of U.S. patent application No. 09/118,627, filed Jul. 17, 1998, which is a continuation-in-part of U.S. patent application No. 08/998,253, filed Dec. 24, 1997, now abandoned.

TECHNICAL FIELD

The present invention relates generally to compositions and methods for the treatment and diagnosis of breast cancer. The invention is more particularly related to polypeptides comprising at least a portion of a protein that is preferentially expressed in breast tumor tissue and to polynucleotides encoding such polypeptides. Such polypeptides and polynucleotides may be used in vaccines and pharmaceutical compositions for treatment of breast cancer. Additionally such polypeptides and polynucleotides may be used in the immunodiagnosis of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

The present invention provides compounds and methods for immunotherapy of breast cancer. In one aspect, isolated polypeptides are provided comprising at least an immunogenic portion of a breast tumor protein or a variant of said protein that differs only in conservative substitutions and/or modifications, wherein the breast tumor protein comprises an amino acid sequence encoded by a polynucleotide comprising a sequence selected from the group consisting of (a) nucleotide sequences recited in SEQ ID NOS: 3, 10, 17, 24, 45–52, 55–67, 72, 73, 89–97, 102 and 107, (b) complements of said nucleotide sequences and (c) sequences that hybridize to a sequence of (a) or (b) under moderately stringent conditions. In specific embodiments, the isolated polypeptides of the present invention comprise an amino acid sequence of SEQ ID NO: 98, 99 or 101.

In related aspects, isolated polynucleotides encoding the above polypeptides are provided. In specific embodiments, such polynucleotides comprise sequences provided in SEQ ID NOS: 3, 10, 17, 24, 45–52 and 55–67, 72, 73, 89–97, 102 and 107. The present invention further provides expression vectors comprising the above polynucleotides and host cells transformed or transfected with such expression vectors. In preferred embodiments, the host cells are selected from the group consisting of *E. coli*, yeast and mammalian cells.

In another aspect, the present invention provides fusion proteins comprising a first and a second inventive polypeptide or, alternatively, an inventive polypeptide and a known breast antigen.

The present invention also provides pharmaceutical compositions comprising at least one of the above polypeptides, or a polynucleotide encoding such a polypeptide, and a physiologically acceptable carrier, together with vaccines comprising at least one or more such polypeptide or polynucleotide in combination with a non-specific immune response enhancer. Pharmaceutical compositions and vaccines comprising one or more of the above fusion proteins are also provided.

In related aspects, pharmaceutical compositions for the treatment of breast cancer comprising at least one polypeptide and a physiologically acceptable carrier are provided, wherein the polypeptide comprises an immunogenic portion of a breast tumor protein or a variant thereof, the breast tumor protein being encoded by a polynucleotide comprising a sequence selected from the group consisting of: (a) nucleotide sequences recited in SEQ ID NOS: 1, 2, 4–9, 11–16, 18–23, 25–44, 53, 54, 68–71, 74–88 and 103–106, (b) complements of said nucleotide sequences, and (c) sequences that hybridize to a sequence of (a) or (b) under moderately stringent conditions. The invention also provides vaccines for the treatment of breast cancer comprising such polypeptides in combination with a non-specific immune response enhancer, together with pharmaceutical compositions and vaccines comprising at least one polynucleotide comprising a sequence provided in SEQ ID NOS: 1, 2, 4–9, 11–16, 18–23, 25–44, 53, 54, 68–71, 74–88 and 103–106.

In yet another aspect, methods are provided for inhibiting the development of breast cancer in a patient, comprising administering an effective amount of at least one of the above pharmaceutical compositions and/or vaccines.

The present invention also provides methods for immunodiagnosis of breast cancer, together with kits for use in such methods. In one specific aspect of the present invention, methods are provided for detecting breast cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of breast cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides methods for detecting breast cancer comprising: (a) obtaining a biological sample from a patient; (b) contacting the sample with a first and a second oligonucleotide primer in a polymerase chain reaction, at least one of the oligonucleotide primers being specific for a polynucleotide that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a polynucleotide comprising a sequence selected from the group consisting of SEQ ID NOS: 1–97, 100 and 102–107.

In a further aspect, the present invention provides a method for detecting breast cancer in a patient comprising: (a) obtaining a biological sample from the patient; (b) contacting the sample with an oligonucleotide probe specific for a polynucleotide that encodes one of the above polypeptides; and (c) detecting in the sample a polynucleotide sequence that hybridizes to the oligonucleotide probe. Preferably, the oligonucleotide probe comprises at least about 15 contiguous nucleotides of a polynucleotide comprising a sequence selected from the group consisting of SEQ ID NOS: 1–97, 100 and 102–107.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWINGS AND SEQUENCE IDENTIFIERS

FIGS. 1A and B show the specific lytic activity of a first and a second B511S-specific CTL clone, respectively, measured on autologous LCL transduced with B511s (filled squares) or HLA-A3 (open squares).

SEQ ID NO: 1 is the determined 3'cDNA sequence of 1T-5120
SEQ ID NO: 2 is the determined 3'cDNA sequence of 1T-5122
SEQ ID NO: 3 is the determined 3'cDNA sequence of 1T-5123
SEQ ID NO: 4 is the determined 3'cDNA sequence of 1T-5125
SEQ ID NO: 5 is the determined 3'cDNA sequence of 1T-5126
SEQ ID NO: 6 is the determined 3'cDNA sequence of 1T-5127
SEQ ID NO: 7 is the determined 3'cDNA sequence of 1T-5129
SEQ ID NO: 8 is the determined 3'cDNA sequence of 1T-5130
SEQ ID NO: 9 is the determined 3'cDNA sequence of 1T-5133
SEQ ID NO: 10 is the determined 3'cDNA sequence of 1T-5136
SEQ ID NO: 11 is the determined 3'cDNA sequence of 1T-5137
SEQ ID NO: 12 is the determined 3'cDNA sequence of 1T-5139
SEQ ID NO: 13 is the determined 3'cDNA sequence of 1T-5142
SEQ ID NO: 14 is the determined 3'cDNA sequence of 1T-5143
SEQ ID NO: 15 is the determined 5'cDNA sequence of 1T-5120
SEQ ID NO: 16 is the determined 5'cDNA sequence of 1T-5122
SEQ ID NO: 17 is the determined 5'cDNA sequence of 1T-5123
SEQ ID NO: 18 is the determined 5'cDNA sequence of 1T-5125
SEQ ID NO: 19 is the determined 5'cDNA sequence of 1T-5126
SEQ ID NO: 20 is the determined 5'cDNA sequence of 1T-5127
SEQ ID NO: 21 is the determined 5'cDNA sequence of 1T-5129
SEQ ID NO: 22 is the determined 5'cDNA sequence of 1T-5130
SEQ ID NO: 23 is the determined 5'cDNA sequence of 1T-5133
SEQ ID NO: 24 is the determined 5'cDNA sequence of 1T-5136
SEQ ID NO: 25 is the determined 5'cDNA sequence of 1T-5137
SEQ ID NO: 26 is the determined 5'cDNA sequence of 1T-5139
SEQ ID NO: 27 is the determined 5'cDNA sequence of 1T-5142
SEQ ID NO: 28 is the determined 5'cDNA sequence of 1T-5143
SEQ ID NO: 29 is the determined 5'cDNA sequence of 1D-4315
SEQ ID NO: 30 is the determined 5'cDNA sequence of 1D-4311
SEQ ID NO: 31 is the determined 5'cDNA sequence of 1E-4440
SEQ ID NO: 32 is the determined 5'cDNA sequence of 1E-4443
SEQ ID NO: 33 is the determined 5'cDNA sequence of 1D-4321
SEQ ID NO: 34 is the determined 5'cDNA sequence of 1D-4310
SEQ ID NO: 35 is the determined 5'cDNA sequence of 1D-4320
SEQ ID NO: 36 is the determined 5'cDNA sequence of 1E-4448
SEQ ID NO: 37 is the determined 5'cDNA sequence of 1S-5105
SEQ ID NO: 38 is the determined 5'cDNA sequence of 1S-5110
SEQ ID NO: 39 is the determined 5'cDNA sequence of 1S-5111
SEQ ID NO: 40 is the determined 5'cDNA sequence of 1S-5116
SEQ ID NO: 41 is the determined 5'cDNA sequence of 1S-5114
SEQ ID NO: 42 is the determined 5'cDNA sequence of 1S-5115
SEQ ID NO: 43 is the determined 5'cDNA sequence of 1S-5118
SEQ ID NO: 44 is the determined 5'cDNA sequence of 1T-5134

SEQ ID NO: 45 is the determined 5'cDNA sequence of 1E-4441
SEQ ID NO: 46 is the determined 5'cDNA sequence of IE-4444
SEQ ID NO: 47 is the determined 5'cDNA sequence of IE-4322
SEQ ID NO: 48 is the determined 5'cDNA sequence of IS-5103
SEQ ID NO: 49 is the determined 5'cDNA sequence of IS-5107
SEQ ID NO: 50 is the determined 5'cDNA sequence of IS-5113
SEQ ID NO: 51 is the determined 5'cDNA sequence of IS-5117
SEQ ID NO: 52 is the determined 5'cDNA sequence of IS-5112
SEQ ID NO: 53 is the determined cDNA sequence of 1013E11
SEQ ID NO: 54 is the determined cDNA sequence of 1013H10
SEQ ID NO: 55 is the determined cDNA sequence of 1017C2
SEQ ID NO: 56 is the determined cDNA sequence of 1016F8
SEQ ID NO: 57 is the determined cDNA sequence of 1015F5
SEQ ID NO: 58 is the determined cDNA sequence of 1017A11
SEQ ID NO: 59 is the determined cDNA sequence of 1013A11
SEQ ID NO: 60 is the determined cDNA sequence of 1016D8
SEQ ID NO: 61 is the determined cDNA sequence of 1016D12
SEQ ID NO: 62 is the determined cDNA sequence of 1015E8
SEQ ID NO: 63 is the determined cDNA sequence of 1015D11
SEQ ID NO: 64 is the determined cDNA sequence of 1012H8
SEQ ID NO: 65 is the determined cDNA sequence of 1013C8
SEQ ID NO: 66 is the determined cDNA sequence of 1014B3
SEQ ID NO: 67 is the determined cDNA sequence of 1015B2
SEQ ID NO: 68–71 are the determined cDNA sequences of previously identified antigens
SEQ ID NO: 72 is the determined cDNA sequence of JJ9434
SEQ ID NO: 73 is the determined cDNA sequence of B535S
SEQ ID NO: 74–88 are the determined cDNA sequence of previously identified antigens
SEQ ID NO: 89 is the determined cDNA sequence of B534S
SEQ ID NO: 90 is the determined cDNA sequence of B538S
SEQ ID NO: 91 is the determined cDNA sequence of B542S
SEQ ID NO: 92 is the determined CDNA sequence of B543S
SEQ ID NO: 93 is the determined cDNA sequence of P501S
SEQ ID NO: 94 is the determined cDNA sequence of B541S
SEQ ID NO: 95 is an extended cDNA sequence for 1016F8 (also referred to as B511S)
SEQ ID NO: 96 is an extended cDNA sequence for 1016D12 (also referred to as B532S)
SEQ ID NO: 97 is an extended cDNA sequence for 1012H8 (also referred to as B533S)
SEQ ID NO: 98 is the predicted amino acid sequence for B511S
SEQ ID NO: 99 is the predicted amino acid sequence for B532S
SEQ ID NO: 100 is the determined full-length cDNA sequence for P501S
SEQ ID NO: 101 is the predicted amino acid sequence for P501S
SEQ ID NO: 102 is the determined cDNA sequence of clone #19605, also referred to as 1017C2, showing no significant homology to any known gene
SEQ ID NO: 103 is the determined 3' end cDNA sequence for clone #19599, showing homology to the Tumor Expression Enhanced gene
SEQ ID NO: 104 is the determined 5' end cDNA sequence for clone #19599, showing homology to the Tumor Expression Enhanced gene
SEQ ID NO: 105 is the determined cDNA sequence for clone #19607, showing homology to Stromelysin-3
SEQ ID NO: 106 is the determined cDNA sequence for clone #19601, showing homology to Collagen
SEQ ID NO: 107 is the determined cDNA sequence of clone #19606, also referred to as B546S, showing no significant homology to any known gene

DETAILED DESCRIPTION OF THE INVENTION

As not ed above, the present invention is generally directed to compositions and methods for the immunotherapy and diagnosis of breast cancer. The inventive compositions are generally isolated polypeptides that comprise at least a portion of a breast tumor protein. Also included within the present invention are molecules (such as an antibody or fragment thereof) that bind to the inventive polypeptides. Such molecules are referred to herein as "binding agents."

In particular, the subject invention discloses isolated polypeptides comprising at least a portion of a human breast tumor protein, or a variant thereof, wherein the breast tumor protein includes an amino acid sequence encoded by a polynucleotide molecule including a sequence selected from the group consisting of: nucleotide sequences recited in SEQ ID NOS: 1–97, 100 and 102–107, the complements of said nucleotide sequences, and variants thereof. In certain specific embodiments, the inventive polypeptides comprise an amino acid sequence selected from the group consisting of sequences provided in SEQ ID NO: 98, 99 and 101, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor protein is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Anti-* bodies: *A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology,* 3$^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. A polypeptide "variant," as used herein, is a polypeptide that differs from the recited polypeptide only in conservative substitutions and/or modifications, such that the therapeutic, antigenic and/or immunogenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, more preferably 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

For breast tumor polypeptides with immunoreactive properties, variants may alternatively be identified by modifying the amino acid sequence of one of the above polypeptides, and evaluating the immunoreactivity of the modified polypeptide. For breast tumor polypeptides useful for the generation of diagnostic binding agents, a variant may be identified by evaluating a modified polypeptide for the ability to generate antibodies that detect the presence or absence of breast cancer. Such modified sequences may be prepared and tested using, for example, the representative procedures described herein.

The breast tumor proteins of the present invention, and polynucleotide molecules encoding such proteins, may be isolated from breast tumor tissue using any of a variety of methods well known in the art. Polynucleotide sequences corresponding to a gene (or a portion thereof) encoding one of the inventive breast tumor proteins may be isolated from a breast tumor cDNA library using a subtraction technique as described in detail below. Examples of such DNA sequences are provided in SEQ ID NOS: 1–97, 100 and 102–107. Partial polynucleotide sequences thus obtained may be used to design oligonucleotide primers for the amplification of full-length polynucleotide sequences in a polymerase chain reaction (PCR), using techniques well known in the art (see, for example, Mullis et al., *Cold Spring Harbor Symp. Quant. Biol.,* 51:263, 1987; Erlich ed., *PCR Technology*, Stockton Press, NY, 1989). Once a polynucleotide sequence encoding a polypeptide is obtained, any of the above modifications may be readily introduced using standard mutagenesis techniques, such as oligonucleotide-directed site-specific mutagenesis as taught, for example, by Adelman et al. (*DNA,* 2:183, 1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a polynucleotide sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli*, yeast or a mammalian cell line, such as CHO cells. The polynucleotide sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known breast tumor antigen, together with variants of such fusion proteins.

A polynucleotide sequence encoding a fusion protein of the present invention is constructed using known recombinant DNA techniques to assemble separate polynucleotide sequences encoding the first and second polypeptides into an appropriate expression vector. The 3' end of a polynucleotide sequence encoding the first polypeptide is ligated, with or without a peptide linker, to the 5' end of a polynucleotide sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotides are located only 5' to the polynucleotide sequence encoding the first polypeptide. Similarly, stop codons required to end translation and transcription termination signals are only present 3' to the polynucleotide sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91 (1997)).

Polypeptides of the present invention that comprise an immunogenic portion of a breast tumor protein may generally be used for immunotherapy of breast cancer, wherein the polypeptide stimulates the patient's own immune response to breast tumor cells. In further aspects, the present invention provides methods for using one or more of the immunoreactive polypeptides encoded by a polynucleotide molecule having a sequence provided in SEQ ID NOS: 1–97, 100 and 102–107 (or fusion proteins comprising one or more such polypeptides and/or polynucleotides encoding such polypeptides) for immunotherapy of breast cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or polynucleotide molecules encoding such polypeptides) may be used to treat breast cancer or to inhibit the development of breast cancer. In a preferred embodiment, the polypeptides are administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain polynucleotides encoding one or more of the above polypeptides, such that the polypeptide is generated in situ. In such pharmaceutical compositions and vaccines, the polynucleotide may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter). Bacterial delivery systems involve the administration of a bacterium (such as Bacillus-Calmette-Guerrin) that expresses an epitope of a breast tumor cell antigen on its cell surface. In a preferred embodiment, the polynucleotide molecules may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating polynucleotides into such expression systems are well known to those of ordinary skill in the art.

The polynucleotides may also be "naked," as described, for example, in published PCT application WO 90/11092, and Ulmer et al., *Science* 259:1745–1749, 1993, reviewed by Cohen, *Science* 259:1691–1692, 1993. The uptake of naked polynucleotides may be increased by coating the polynucleotides onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the polynucleotide in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast or B-cells, may be pulsed with immunoreactive polypeptides or polynucleotide sequence(s) may be introduced into antigen presenting cells, using standard techniques well known in the art. For example, antigen presenting cells may be transfected or transduced with a polynucleotide sequence, wherein said sequence contains a promoter region appropriate for inducing expression, and can be expressed as part of a recombinant virus or other expression system. Several viral vectors may be used to transduce an antigen presenting cell, including pox virus, vaccinia virus, and adenovirus. Antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews,* 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.,* 22(3), 213, 1996). Cells of the immune system, such as T cells, may be isolated from the peripheral blood of a patient, using a commercially available cell separation system. The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother,* 45(3–4):131–6, 1997 and Hwu, P., et al, *Cancer Res,* 55(15) :3369–73, 1995. Another embodiment may include the transfection of tumor antigen specific alpha and beta T cell receptor chains into alternate T cells, as in Cole, D J, et al, *Cancer Res,* 55(4):748–52, 1995.

In further embodiments, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. (*Immunological Reviews,* 157:177, 1997).

Additionally, vectors expressing the disclosed polynucleotides may be introduced into stem cells taken from the patient and clonally propagated in vitro for autologous transplant back into the same patient.

In one specific embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor protein, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor proteins are portions that are able to generate a binding agent that indicates the presence of primary or metastatic breast cancer in substantially all (i.e., at least about 80%, and preferably at least about 90%) of the patients for which breast cancer would be indicated using the full length protein, and that indicate the absence of breast cancer in substantially all of those samples that would be negative when tested with full length protein. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides, relative to a predetermined cut-off value. As used herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%—specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment, assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g. covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a to linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise at least a portion of a polynucleotide disclosed herein. For example, at least two oligonucleotide primers may be employed in a polymerase chain reaction (PCR) based assay to amplify breast tumor-specific cDNA derived from a biological sample, wherein at least one of the oligonucleotide primers is specific for a polynucleotide encoding a breast tumor protein of the present invention. The presence of the amplified cDNA is then detected using techniques well known in the art, such as gel electrophoresis. Similarly, oligonucleotide probes specific for a polynucleotide encoding a breast tumor protein of the present invention may be used in a hybridization assay to detect the presence of an inventive polypeptide in a biological sample.

As used herein, the term "oligonucleotide primer/probe specific for a polynucleotide" means an oligonucleotide sequence that has at least about 60%, preferably at least about 75% and more preferably at least about 90%, identity to the polynucleotide in question, or an oligonucleotide sequence that is anti-sense to a sequence that has at least about 60%, preferably at least about 75% and more preferably at least about 90%, identity to the polynucleotide in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide disclosed herein or that is anti-sense to a polynucleotide sequence disclosed herein. Preferably, oligonucleotide probes for use in the inventive diagnostic methods comprise at least about 15 contiguous oligonucleotides of a polynucleotide that encodes one of the polypeptides disclosed herein or that is anti-sense to a sequence that encodes one of the polypeptides disclosed herein. Techniques for both PCR based assays and hybridization assays are well known in the art (see, for example, Mullis et al. Ibid; Ehrlich, Ibid). Primers or probes may thus be used to detect breast tumor-specific sequences in biological samples, including blood, urine and/or breast tumor tissue.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A human breast tumor cDNA expression library was constructed from a pool of breast tumor poly $A^{30}$ RNA from three patients using a Superscript Plasmid System for cDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly $A^{30}$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BstX I adaptors (Invitrogen, Carlsbad, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen, Carlsbad, Calif.) and transformed into ElectroMax E. coli DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. The breast tumor library contained $1.14 \times 10^7$ independent colonies, with more than 90% of clones having a visible insert and the average insert size being 936 base pairs. The normal breast cDNA library contained $6 \times 10^6$ independent colonies, with 83% of clones having inserts and the average insert size being 1015 base pairs. Sequencing analysis showed both libraries to contain good complex cDNA clones that were synthesized from mRNA, with minimal rRNA and mitochondrial DNA contamination sequencing.

cDNA library subtraction was performed using the above breast tumor and normal breast CDNA libraries, as described by Hara et al. (*Blood*, 84:189–199, 1994) with some modifications. Specifically, a breast tumor-specific subtracted cDNA library was generated as follows. Normal breast cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of Photoprobe biotin (Vector Laboratories, Burlingame, Calif.), the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl H$_2$O to form the driver DNA.

To form the tracer DNA, 10 μg breast tumor cDNA library was digested with BamHI and XhoI, phenol chloroform extracted and passed through Chroma spin-400 columns (Clontech). Following ethanol precipitation, the tracer DNA was dissolved in 5 μl H$_2$O. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl H$_2$O, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax E. coli DH10B cells by electroporation to generate a breast tumor specific subtracted cDNA library.

To analyze the subtracted cDNA library, plasmid DNA was prepared from 100 independent clones, randomly picked from the subtracted breast tumor specific library and characterized by DNA sequencing with a Perkin Elmer/Applied Biosystems Division Automated Sequencer Model 373A (Foster City, Calif.). Thirty-eight distinct cDNA clones were found in the subtracted breast tumor-specific cDNA library. The determined 3' cDNA sequences for 14 of these clones are provided in SEQ ID NO: 1–14, with the corresponding 5' cDNA sequences being provided in SEQ ID NO: 15–28, respectively. The determined one strand (5' or 3') cDNA sequences for the remaining clones are provided in SEQ ID NO: 29–52. Comparison of these cDNA sequences with known sequences in the gene bank using the EMBL and GenBank databases (Release 97) revealed no significant homologies to the sequences provided in SEQ ID NO: 3, 10, 17, 24 and 45–52. The sequences provided in SEQ ID NO: 1, 2, 4–9, 11–16, 18–23, 25–41, 43 and 44 were found to show at least some degree of homology to known human genes. The sequence of SEQ ID NO: 42 was found to show some homology to a known yeast gene.

cDNA clones isolated in the breast subtraction described above were colony PCR amplified and their mRNA expression levels in breast tumor, normal breast and various other normal tissues were determined using microarray technology (Synteni, Fremont, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity.

Data was analyzed using GEMTOOLS Software. Twenty one distinct cDNA clones were found to be over-expressed in breast tumor and expressed at low levels in all normal tissues tested. The determined partial cDNA sequences for these clones are provided in SEQ ID NO: 53–73. Comparison of the sequences of SEQ ID NO: 53, 54 and 68–71 with those in the gene bank as described above, revealed some homology to previously identified human genes. No significant homologies were found to the sequences of SEQ ID NO: 55–67, 72 (referred to as JJ 9434) and 73 (referred to as B535S). In further studies, full length cDNA sequences were obtained for the clones 1016F8 (SEQ ID NO: 56; also referred to as B511S) and 1016D12 (SEQ ID NO: 61; also referred to as B532S), and an extended cDNA sequence was obtained for 1012H8 (SEQ ID NO: 64; also referred to as B533S). These cDNA sequences are provided in SEQ ID NO: 95–97, respectively, with the corresponding predicted amino acid sequences for B511S and B532S being provided in SEQ ID NO: 98 and 99, respectively.

Analysis of the expression of B511S in breast tumor tissues and in a variety of normal tissues (skin, PBMC, intestine, breast, stomach, liver, kidney, fetal tissue, adrenal gland, salivary gland, spinal cord, large intestine, small intestine, bone marrow, brain, heart, colon and pancreas) by microarray, northern analysis and real time PCR, demonstrated that B511S is over-expressed in breast tumors, and normal breast, skin and salivary gland, with expression being low or undetectable in all other tissues tested.

Analysis of the expression of B532S in breast tumor tissue and in a variety of normal tissues (breast, PBMC, esophagus, HMEC, spinal cord, bone, thymus, brain, bladder, colon, liver, lung, skin, small intestine, stomach, skeletal muscle, pancreas, aorta, heart, spleen, kidney, salivary gland, bone marrow and adrenal gland) by microarray, Northern analysis and real time PCR, demonstrated that B532S is over-expressed in 20–30% of breast tumors with expression being low or undetectable in all other tissues tested.

In a further experiment, cDNA fragments were obtained from two subtraction libraries derived by conventional subtraction, as described above and analyzed by DNA microarray. In one instance the tester was derived from primary breast tumors, referred to as Breast Subtraction 2, or BS2. In the second instance, a metastatic breast tumor was employed as the tester, referred to as Breast Subtraction 3, or BS3. Drivers consisted of normal breast.

cDNA fragments from these two libraries were submitted as templates for DNA microarray analysis, as described above. DNA chips were analyzed by hybridizing with fluorescent probes derived from mRNA from both tumor and normal tissues. Analysis of the data was accomplished by creating three groups from the sets of probes, referred to as breast tumor/mets, normal non-breast tissues, and metastatic breast tumors. Two comparisons were performed using the modified Gemtools analysis. The first comparison was to identify templates with elevated expression in breast tumors. The second was to identify templates not recovered in the first comparison that yielded elevated expression in metastatic breast tumors. An arbitrary level of increased expression (mean of tumor expression versus the mean of normal tissue expression) was set at approximately 2.2.

In the first round of comparison to identify over-expression in breast tumors, two novel gene sequences were identified, hereinafter referred to as B534S and B538S (SEQ ID NO: 89 and 90, respectively), together with six sequences that showed some degree of homology to previously identified genes (SEQ ID NO: 74–79). The sequences of SEQ ID NO: 75 and 76 were subsequently determined to be portions of B535S (SEQ ID NO: 73). In a second comparison to identify elevated expression in metastatic breast tumors, five novel sequences were identified, hereinafter referred to as B535S, B542S, B543S, P501S and B541S (SEQ ID NO: 73 and 91–94, respectively), as well as nine gene sequences that showed some homology to known genes (SEQ ID NO: 80–88). Clone B534S and B538S (SEQ ID NO: 89 and 90) were shown to be over-expressed in both breast tumors and metastatic breast tumors.

In a subsequent series of studies, 457 clones from Breast Subtraction 2 were analyzed by microarray on Breast Chip 3. As described above, a first comparison to identify over-expression in breast tumors over normal non-breast tissues was performed. This analysis yielded six cDNA clones that demonstrated elevated expression in breast tumor over normal non-breast tissues. Two of these clones, referred to as 1017C2 (SEQ ID NO: 102) and B546S (SEQ ID NO: 107) do not share significant homology to any known genes. Clone B511S also showed over-expression in breast tumor, which was previously described as 1016F8, with the determined cDNA sequence provided in SEQ ID NO: 95 and the predicted amino acid sequence provided in SEQ ID NO: 98. The remaining four clones over-expressed in breast tumor were found to share some degree of homology to Tumor Expression Enhanced Gene (SEQ ID NO: 103 and 104) Stromelysin-3 (SEQ ID NO: 105) or Collagen (SEQ ID NO: 106).

In the second comparison to determine genes with elevated expression in metastatic breast tumors over non-breast normal tissues, a profile similar to the first comparison was derived. The two putatively novel clones, 1017C2 and B546S, SEQ ID NO: 102 and 107, respectively, were overexpressed in metastatic breast tumors. In addition, Tumor Expression Enhanced Gene and B511S also showed elevated expression in metastatic breast tumors.

As described in U.S. patent application Ser. No. 08/806,099, filed Feb. 25, 1997, the antigen P501S was isolated by subtracting a prostate tumor cDNA library with a normal pancreas cDNA library and with three genes found to be abundant in a previously subtracted prostate tumor specific cDNA library: human glandular kallikrein, prostate specific antigen (PSA), and mitochondria cytochrome C oxidase subunit II. The determined full-length cDNA sequence for P501S is provided in SEQ ID NO: 100, with the corresponding predicted amino acid sequence being provided in SEQ ID NO: 101. Expression of P501S in breast tumor was examined by microarray analysis. Over-expression was found in prostate tumor, breast tumor and metastatic breast tumor, with negligible to low expression being seen in normal tissues. This data suggests that P501S may be over-expressed in various breast tumors as well as in prostate tumors.

Example 2

Generation of Human CD8+ Cytotoxic T-cells that Recognize Antigen Presenting Cells Expressing Breast Tumor Antigens This Example illustrates the generation of T cells that recognize target cells expressing the antigen B511S, also known as 1016-F8 (SEQ ID NO: 56). Human CD8+ T cells were primed in-vitro to the B511S gene product using dendritic cells infected with a recombinant vaccinia virus engineered to express B511S as follows (also see Yee et al., Journal of Immunology (1996) 157 (9):4079–86). Dendritic cells (DC) were generated from peripheral blood derived monocytes by differentiation for 5 days in the presence of 50 µg/ml GMCSF and 30 µg/ml IL-4. DC were harvested, plated in wells of a 24-well plate at a density of 2×10$^5$ cells/well and infected for 12 hours with B511S expressing vaccinia at a multiplicity of infection of 5. DC were then matured overnight by the addition of 3 µg/ml CD40-Ligand and UV irradiated at 100 µW for 10 minutes. CD8+ T cells were isolated using magnetic beads, and priming cultures were initiated in individual wells (typically in 24 wells of a 24-well plate) using 7×10$^5$ CD8+ T cells and 1×10$^6$ irradiated CD8-depleted PBMC. IL-7 at 10 ng/ml was added to cultures at day 1. Cultures were re-stimulated every 7–10 days using autologous primary fibroblasts retrovirally transduced with B511S and the costimulatory molecule B7.1. Cultures were supplemented at day 1 with 15 I.U. of IL-2. Following 4 such stimulation cycles, CD8+ cultures were tested for their ability to specifically recognize autologous fibroblasts transduced with B511S using an interferon-γ Elispot assay (see Lalvani et al J. Experimental Medicine (1997) 186:859–965). Briefly, T cells from individual microcultures were added to 96-well Elispot plates that contained autologous fibroblasts transduced to express either B511S or as a negative control antigen EGFP, and incubated overnight at 37° C.; wells also contained IL-12 at 10 ng/ml. Cultures were identified that specifically produced interferon-γ only in response to B511S transduced fibroblasts; such lines were further expanded and also cloned by limiting dilution on autologous B-LCL retrovirally transduced with B511S. Lines and clones were identified that could specifically recognize autologous B-LCL transduced with B511S but not autologous B-LCL transduced with the control antigens EGFP or HLA-A3. An example demonstrating the ability of human CTL cell lines derived from such experiments to specifically recognize and lyse B511S expressing targets is presented in FIG. 1.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An insolated polypeptide comprising SEQ ID NO:99.
2. A composition comprising a polypeptide of claim 1 and a physiologically acceptable carrier.
3. A composition comprising a polypeptide of claim 1 and a non-specific immune response enhancer.
4. The composition of claim 3 wherein the non-specific immune response enhancer is an adjuvant.
5. A fusion protein comprising at least one polypeptide according to claim 1.
6. A composition comprising a fusion protein according to claim 5 and a physiologically acceptable carrier.
7. A composition comprising a fusion protein according to claim 5 and a non-specific immune response enhancer.
8. The composition of claim 7 wherein the non-specific immune response enhancer is an adjuvant.
9. An isolated polypeptide comprising an amino acid sequence encoded by SEQ ID NO: 96.

* * * * *

SEQUENCE LISTING

<160> NUMBER OF SEQ ID NOS: 107

<210> SEQ ID NO 1
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 1

```
tttttttttt tttttaggag aactgaatca aacagatttt attcaacttt t tagatgagg      60
aaaacaaatn atacgaaatn ngtcataaga aatgctttct tataccacta t ctcaaacca    120
ctttcaatat tttacaaaat gctcacgcag caaatatgaa aagctncaac a cttcccttt    180
gttaacttgc tgcaatnaat gcaactttaa canacataca aatttcttct g tatcttaaa    240
agttnaatta ctaattttaa tgatnttnct caagatnttt attcatatac t tttaatgac    300
tcnttgccna tacatacnta ttttctttac tttttttta cnatnggcca a cagctttca    360
ngcagnccnc aaaaatctta ccggttaatt acacggggtt gt                       402
```

<210> SEQ ID NO 2
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 2

```
tttttttttt tttttaaag gtacacattt cttttcatt ctgtttnatg c agcaaataa      60
ttcgttggca tcttctctgt gatgggcagc ttgctaaaat tanactcagg c cccttagct   120
ncatttccaa ctnagcccac gctttcaacc nngccnaaca aagaaaatca g ttngggtta   180
aattctttgc tgganacaaa gaactacatt cctttgtaaa tnatgctttg t ttgctctgt   240
gcaaacncag attgaaggga anaagganac ttntggggac ggaaacaact n gnagaagca   300
gganccgccc agggncattt cctcaccatg cttaatcttg cnctcacttg c nggcacca    360
ttaaacttgg tgcaaaaggc gcaattggtg nanggaaccc cacaccttcc t taaaaagca   420
gggc                                                                424
```

<210> SEQ ID NO 3
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 3

```
tttttttttt tttttcccaa tttaaaaaag cctttttcat acttcaatta c accanactt    60
aatnatttca tgagtaaatc ngacattatt atttnaaaat ttgcatattt a aaatttgna   120
tcanttactt ccagactgtt tgcanaatga agggaggatc actcaagngc t gatctcnca   180
ctntctgcag tctnctgtcc tgtgcccggn ctaatggatc gacactanat g gacagntcn   240
cagatcttcc gttcttntcc cttccccaat ttcncaccnc tcccttctt n cccggatcn    300
```

```
tttggggaca tgntaattt gcnatcctta aaccctgccc gccangggtc c cnanctcag       360 gggtggttaa tgttcgncng gcttnttgac cncctgcgcc ctttnantcc n aaccccaag     420 c                                                                       421
```

<210> SEQ ID NO 4
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 4

```
ttttttatt ttttttcta tttntnntat ttnntgnggt tcctgtgtgt a attagnang       60 tgtgtatgcg tangtacnta tgtntgcata tttaacctgt tnccttcca t ttttaaaat      120 aaaatctcaa natngtantt ggttnatggg agtaaanaga gactatngat n aattttaac    180 atggacacng tgaaatgtag ccgctnatca ntttaaaact tcattttgaa g gccttttnc    240 cctccnaata aaaatnccng gccctactgg gttaagcaac attgcatntc t aaagaaacc    300 acatgcananc nagttaaacc tgtgnactgg tcangcaaac cnanntggaa n anaagggnn   360 ttcncccan ggacantcng aattttttta acaaattacn atncccccc n ggggagcc      420 tgt                                                                    423
```

<210> SEQ ID NO 5
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 5

```
acgaccacct natttcgtat ctttcaactc ttttcgaccg gacctcttat t cggaagcgt    60 tccaggaaga caggtctcaa cttagggatc agatcacgtt atcaacgctc t gggatcgct  120 gcaacctggc acttcaagga agtgcaccga tnacgtctag accggccaac a cagatctag  180 aggtggccaa ctgatcactg taggagctga ctggcaaanan tcaaccgggc c ccaaccnag 240 agtgaccaan acnaccattn aggatcaccc acaggcactc ctcgtcctag g gccaaccna 300 ccaaacggct ggccaatggg ggggtttaat atttggttna aaaattgatt t taaa       355
```

<210> SEQ ID NO 6
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 6

```
ttttttttt tttttggaca ggaagtaaaa tttattggtn antattaana g ggggggcagc    60 acattggaag ccctcatgan tgcagggccc gccacttgtc cagagggcca c nattgggga  120 tgtacttaac cccacagccn tctgggatna gccgctttc agccaccatn t cttcaaatt   180 catcagcatt aaacttggta aancccact tctttaagat ntgnatcttc t ggcggccag   240
```

-continued

```
naaacttgaa cttggccctg cgcagggcct caatcacatg ctccttgttc t gcagcttgg      300 tgcgnaagga cntaatnact tggccnatgt gaaccctggc cacantgccc t ggggcttc      360 caaaggcacc tcgcaagcct ntttggancc tgnccgcccc ngcacaggga c aacatcttg    420 ttt                                                                    423
```

<210> SEQ ID NO 7
<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 7

```
ttcgcactgg ctaaaacaaa ccgccttgca aagttngaaa aatttatcaa t ggaccaaat      60 aatgctcata tccnacaagt tggtgaccgt tnttatnata aaaaaatgta t natgctcct    120 nanttgttgt acaataatgt tccaattng gacnttcggc atctaccctg g ttcacctgg    180 gtaaatatca ggcagctttt gatggggcta ggaaagctaa cagtactcga a catgggaaa    240 gaggtctgct tcgccngtgt anatgggaaa naattccgtc ttgctcngat t tgtggactt    300 catattgttg tacatgcaga tgaatnngaa gaacttgtca actactatca g gatcgtggc    360 tttttnnaaa agctnatcac catgttggaa gcggcactng gacttgagcg               410
```

<210> SEQ ID NO 8
<211> LENGTH: 274
<212> TYPE: DNA
<213> ORGANISM: Homo sapien
<220> FEATURE:
<221> NAME/KEY: misc_feature
<222> LOCATION: (1)...(274)
<223> OTHER INFORMATION: n = A,T,C or G

<400> SEQUENCE: 8

```
tttttttttt ttttaggtc atacatattt tttattataa canatatntg t atatacata      60 taatatatgt gtatatatcc acgtgtgtgt gtgtgtatca aaaacaacan a antttagtg    120 atctatatct ntngctcaca tatgcatggg agataccagt aaaaaataag t naatctcca    180 taatatgttt taaaactcan anaaatcnga gagactnaaa gaaaacgttn a tcannatga    240 ttgtngataa tcttgaanaa tnacnaaaac atat                                 274
```

<210> SEQ ID NO 9
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 9

```
tttttttttt ttttgtgcct tattgcaccg gcnanaactt ctagcactat a ttaaactca      60 ataagagtga taagtgtgaa aatccttgcc ttctctttaa tcttaatgna n aggcatctg    120 gtttttcacc attaantgta ataatggctn tatgtatttt tatnnatggt c ttnatggag    180 ttaaaaaagt tttcctctnt ccctngttat ctaanagttt tnatcaaaaa t gggtataat    240 atttngttca gtacttttnc ctgcacctat agatatgatn ctgttatttt t tcttcttng    300 cctnnanata tgatggatna ca                                              322
```

<210> SEQ ID NO 10
<211> LENGTH: 425
<212> TYPE: DNA
<213> ORGANISM: Homo sapien
<220> FEATURE:
<221> NAME/KEY: misc_feature
<222> LOCATION: (1)...(425)
<223> OTHER INFORMATION: n = A,T,C or G

<400> SEQUENCE: 10

```
ttttttttttt tttttattct gcagccatta aatgctgaac actagatnct t atttgtgga      60
ggtcacaaaa taagtacaga atatnacaca cgccctgccc ataaaagca c agctcccag       120
ttctatattt acaatatctc tggaattcca ccttcccttc taatttgact a atatttctg     180
cttctcaggc agcagcgcct tctggcaacc ataagaacca acntgnggac t aggtcggtg     240
ggccaaggat caggaaacag aanaatggaa gnagcccccn tgacnctatt a anctntnaa     300
actatctnaa ctgctagttt tcaggcttta aatcatgtaa natacgtgtc c ttnttgctg    360
caaccggaag catcctagat ggtacactct ctccaggtgc caggaaaaga t cccaaatng    420
caggn                                                                   425
```

<210> SEQ ID NO 11
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 11

```
ttttnttant tttttttance nctnntccnn tntgttgnag ggggtaccaa a tttctttat     60
ttaaaggaat ggtacaaatc aaaaaactta atttaattttt tnggtacaac t tatagaaaa   120
ggttaaggaa accccaacat gcatgcactg ccttggtaac cagggnattc c cccncggct   180
ntggggaaat tagcccaang ctnagctttc attatcactn tccccaggg t ntgcttttc    240
aaaaaaattt nccgccnagc cnaatccggg cnctcccatc tggcgcaant t ggtcacttg   300
gtccccccnat tctttaangg cttncacctn ctcattcggg tnatgtgtct c aattaaatc   360
ccacngatgg gggtcatttt tntcnnttag ccagtttgtg nagttccgtt a ttganaaaa   420
ccan                                                                   424
```

<210> SEQ ID NO 12
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 12

```
tttttttttt tttncttaa aagctttat ctcctgctta cattacccat c tgttcttgc      60
atgttgtctg cttttttccac tagagcccct aacaacttaa tcatggttat t ttaagggct  120
ctaataattc cnaaactggt atcataaata agtctcgttc tnatgcttgt t ttctctcta   180
tcacactgtg ttngttgctt tttnacatgc tttgtaattt ttggctgaaa g ctgaaaaat   240
nacataccctg gttntacaac ctgaggtaan cagccttnta gtgtgaggtt t tatatntta  300
```

-continued

| ctggctaaga gctnggcnct gttnantant tgttgtanct ntatatgcca n aggctttna | 360 |
| tttccnctng tgtccttgct tnagtacccc attnttttag gggttccta n aaactctat | 420 |
| ctnaat | 426 |

<210> SEQ ID NO 13
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 13

| ttttttttttt tttttnagat agactctcac tctttcgccc aggctggagt g cagtggcgc | 60 |
| aatcaaggct cactgcaacc tctgccttat aaagcatttn ctaaaggtac a agctaaatt | 120 |
| ttaaaaatat ctctncacaa ctaatgtata acaaaaatta gttctacctc a taaacncnt | 180 |
| ggctcagccc tcgnaacaca tttccctgtt ctcaactgat gaacactcca n aaacagaac | 240 |
| anatntaagc ttttccaggc ccagaaaagc tcgcgagggg atttgctntg t gtgtgacac | 300 |
| acttgccacc ctgtggcagc acagctccac acntgctttg gccgcatttt g caagttctc | 360 |
| tgtaanccc ctgnaagacc cggatcagct gggtngaaat tgcangcnct c ttttggca | 419 |

<210> SEQ ID NO 14
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 14

| aanccattgc caagggtatc cggaggattg tggctgtcac aggtnccgag g cccanaagg | 60 |
| ccctcaggaa agcaaagagc ttgaaaaatg tctctctgtc atggaagcc a agtgaaggc | 120 |
| tcanactgct ccaacaagga tntgcanagg gagatcgcta accttggaga g ccctggcc | 180 |
| actgcagtcn tccccantg gcagaaggat gaattgcggg agactctcan a tcccttang | 240 |
| gaaggtcgtg gatnacttgg accgagcctc nnaagccaat ntccagaaca a gtgttggag | 300 |
| aagacaaagc anttcatcga cgccaacccc naccggcctc tnttctcctg g anattgana | 360 |
| gcggcgcccc cgcccagggc cttaataanc cntgaagctn | 400 |

<210> SEQ ID NO 15
<211> LENGTH: 395
<212> TYPE: DNA
<213> ORGANISM: Homo sapien
<220> FEATURE:
<221> NAME/KEY: misc_feature
<222> LOCATION: (1)...(395)
<223> OTHER INFORMATION: n = A,T,C or G

<400> SEQUENCE: 15

| tgctttgctg cgtccaggaa gattagatng aanaatacat attgatttgc c aaatgaaca | 60 |
| agcgagatta gacntactga anatccatgc aggtcccatt acaaagcatg g tgaaataga | 120 |
| tgatgaagca attgtgaagc tatcggatgg ctttnatgga gcagatctga g aaatgtttg | 180 |
| tactgaagca ggtatgttcg caattcgtgc tgatcatgat tttgtagtac a ggaagactt | 240 |
| catgaaagcn gtcagaanag tggctnattc tnaaagctgg agtctaaatt g gacnacnac | 300 |

```
ctntgtattt actgttggan ttttgatgct gcatgacaga ttttgcttan t gtaaaaatn        360 aagttcaaga aaattatgtt agttttggcc attat                                   395
```

<210> SEQ ID NO 16
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 16

```
ccaccactaa atcctggct gagccctacn agtacctgtg cccctccccc a ggacgagat        60 nagggcacac cctttaagtn aggtgacagg tcacctttaa gtgaggacag t cagctnaat      120 ttcacctctt gggcttgagt acctggttct cgtgccctga ggcgacnctn a gccctgcag      180 ctnccatgta cgtgctgcca atngtcttga tcttctccac gccnctnaac t tgggcttca     240 gtaggagctg caggcnagaa ngaagcggtt aacagcgcca ctccatagcc g cagccnggc     300 tgcccctgct tctcaaggag gggtgtgggg ttcctccacc atcgccgccc t tgcaaacac     360 ntctcanggc ttccctnccg gctnancgca ngacttaagc atgg                         404
```

<210> SEQ ID NO 17
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 17

```
ggccagaagc tttccacaaa ccagtgaagg tggcagcaaa gaaagcctct t agacnagga      60 gctggcagca gctgctatct ngatngacng cagaaaccaa ccactaattc a gcaaacaca    120 acctcatacc tnaccgcttc cctttnaatg gccttcggtg tgtgcgcaca t gggcacgtg    180 cggggagaac catacttatt cccctnttcc cggcctacca cctctnctcc c ccttctctt    240 ctctncaatt actntctccn ctgctttntt ctnancacta ctgctngtnt c nanagccng  300 cccgcaatta cctggcaaaa ctcgcgaccc ttcgggcagc gctaaanaat g cacatttac   360
```

<210> SEQ ID NO 18
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 18

```
atacatatac acatatatga ttttagatag agccatatac ctngaagtag t anatttgtt     60 tgtgtgtata tgtatgtgtc tactcatttt aaataaactt gtgatagaga t gtaattntg    120 agccagtttt tcatttgctt aaatnactca ccaagtaact aattaagttn t ctttactct    180 taatgttnag tagtgagatt ctgttgaagg tgatattaaa aaccattcta t attaattaa    240 cattcatgtt gttttttaaa agcttatttg aaatcnaatt atgattattt t tcataccag   300 tcgatnttat gtangt                                                       316
```

<210> SEQ ID NO 19
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 19

| | | | | | |
|---|---|---|---|---|---|
| aagggatgca | nataatgctg | tgtatgagct | tgatggaaaa | gaactctgta g | tgaaagggt   60 |
| tactattgaa | catgctnggg | ctcggtcacg | aggtggaaga | ggtagaggac g | atactctga  120 |
| ccgttttagt | agtcgcagac | ctcgaaatga | tagacgaaat | gctccacctg t | aagaacaga  180 |
| anatcgtctt | atagttgaga | atttatcctc | aagagtcagc | tggcaggttt g | ttganatac  240 |
| agttttgagt | tnttttgatg | tggcttttta | aaaaagttat | gggttactna t | gttatattg  300 |
| ttttattaaa | agtagttttn | aattaatgga | tntgatggaa | ttgttgtttt |  350 |

<210> SEQ ID NO 20
<211> LENGTH: 367
<212> TYPE: DNA
<213> ORGANISM: Homo sapien
<220> FEATURE:
<221> NAME/KEY: misc_feature
<222> LOCATION: (1)...(367)
<223> OTHER INFORMATION: n = A,T,C or G

<400> SEQUENCE: 20

| | | | | | |
|---|---|---|---|---|---|
| gntnnncnca | agatcctnct | ntccccncgg | gcngccccnc | cnccngtnat n | accggtttn   60 |
| ntaanatcnn | gccgcncccg | aagtctcnct | nntgccgaga | tgncccttat n | cncnnatgn  120 |
| ncaattntga | cctnnggcga | anaatggcng | nngtgtatca | gtntccnctc t | gnggnctct  180 |
| tagnatctga | ccactangac | ccnctatcct | ctcaaaccct | gtanncngcc c | taatttgtg  240 |
| ccaattagtg | catgntanag | cntcctggcc | cagatggcnt | ccatatcctg g | tncggcttc  300 |
| cgcccctacc | angncatccn | catctactag | agcttatccg | ctncntgngg c | gcaccggnt  360 |
| ccccnct |  |  |  |  | 367 |

<210> SEQ ID NO 21
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 21

| | | | | | |
|---|---|---|---|---|---|
| cccaacacaa | tggtctaagt | anaactgtat | tgctctgtag | tatagttcca c | attggcaac   60 |
| ctacaatggg | aaaatccata | cataagtcag | ttacttcctn | atgagctttc t | ccttctgaa  120 |
| tcctttatct | tctgaagaaa | gtacacacct | tggtnatgat | atctttgaat t | gcccttctt  180 |
| tccaggcatc | agttggatga | ttcatcatgg | taattatggc | attatcatat t | cttcatact  240 |
| tgtcatacga | aaacaccagt | tctgcccnna | gatgagcttg | ttctgcagct c | ttagcacct  300 |
| tgggaatatt | cactctagac | cagaaacagc | tcccggtgct | ccctcatttt c | tgaggctta  360 |
| aattn |  |  |  |  | 366 |

<210> SEQ ID NO 22
<211> LENGTH: 315

```
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 22
acttaatgca atctctggag gataaatttgg atcaagaaat aaagaanaaa t gaattagga      60 gaagaaatna ctgggtnata tttcaatatt ttagaacttt aanaatgttg a ctatgattt     120 caatatattt gtnaaaactg agatacangt ttgacctata tctgcatttt g ataattaaa     180 cnaatnnatt ctatttnaat gttgtttcag agtcacagca cagactgaaa c ttttttga      240 atacctnaat atcacacttn tncttnnaat gatgttgaag acaatgatga c atgccttna     300 gcatataatg tcgac                                                       315

<210> SEQ ID NO 23
<211> LENGTH: 202
<212> TYPE: DNA
<213> ORGANISM: Homo sapien
<220> FEATURE:
<221> NAME/KEY: misc_feature
<222> LOCATION: (1)...(202)
<223> OTHER INFORMATION: n = A,T,C or G

<400> SEQUENCE: 23
actaatccag tgtggtgnaa ttccattgtg ttgggcaact caggatatta a atttatnat      60 ttaaaaattc ccaagagaaa naaactccag gccctgattg tttcactggg g aattttacc    120 aaatgttnca nnaaganatg acgctgattc tgtnaaatct ttttcagaag a tagaggaga    180 acacccaccg nttcatttta tg                                               202

<210> SEQ ID NO 24
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 24
ggatttcttg ccctttctc cctttttaag tatcaatgta tgaaatccac c tgtaccacc      60 ctttctgcca tacaaccgct accacatctg gctcctagaa cctgttttgc t ttcatagat    120 ggatctcgga accnagtgtt nacttcattt ttaaacccca ttttagcaga t ngtttgctn    180 tggtctgtct gtattcacca tggggcctgt acacaccacg tgtggttata g tcaaacaca    240 gtgccctcca ttgtggccac atgggagacc catnacccna tactgcatcc t gggctgatn    300 acggcactgc atctnacccg acntgggatt gaacccgggg tgggcagcng a attgaacag    360 gatca                                                                  365

<210> SEQ ID NO 25
<211> LENGTH: 359
<212> TYPE: DNA
<213> ORGANISM: Homo sapien
<220> FEATURE:
<221> NAME/KEY: misc_feature
<222> LOCATION: (1)...(359)
<223> OTHER INFORMATION: n = A,T,C or G

<400> SEQUENCE: 25
```

-continued

| | |
|---|---|
| gtttcctgct tcaacagtgc ttggacggaa cccggcgctc gttccccacc c cggccggcc | 60 |
| gcccatagcc agccctccgt cacctcttca ccgcaccctc ggactgcccc a aggcccccg | 120 |
| ccgccnctcc ngcgccncgc agccaccgcc gccnccncca cctctccttn g tcccgccnt | 180 |
| nacaacgcgt ccacctcgca ngttcgccng aactaccacc nggactcata n gccgccctc | 240 |
| aaccgcccga tcaacctgga gctctncccc ccgacnttaa cctttccntg t cttacttac | 300 |
| nttaaccgcc gnttattttg cttnaaaaga acttttcccc aatactttct t tcaccnnt | 359 |

<210> SEQ ID NO 26
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 26

| | |
|---|---|
| agtgaaacag tatatgtgaa aaggagtttg tgannagcta cataaaaata t tagatatct | 60 |
| ttataatttc caataggata ctcatcagtt ttgaataana gacatattct a gagaaacca | 120 |
| ggtttctggt ttcagatttg aactctcaag agcttggaag ttatcactcc c atcctcacg | 180 |
| acnacnaana aatctnaacn aacngaaaac caatgacttt tcttagatct g tcaaagaac | 240 |
| ttcagccacg aggaaaacta tcnccctnaa tactggggac tggaaagaga g ggtacagag | 300 |
| aatcacagtg aatcatagcc caagatcagc ttgcccggac ctnaagctng t acgatnatt | 360 |
| acttacaggg accacttcac agtnngtnga tnaantgccn | 400 |

<210> SEQ ID NO 27
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 27

| | |
|---|---|
| gaatttctta gaaactgaag tttactctgt tccaagatat atcttcactg t cttaatcaa | 60 |
| agggcgctng aatcatagca aatattctca tctttcaact aactttaagt a gttntcctg | 120 |
| gaattttaca ttttccagaa aacactcctt tctgtatctg tgaaagaaag t gtgcctcag | 180 |
| gctgtagact gggctgcact ggacacctgc gggggactct ggctnagtgn g gacatggtc | 240 |
| agtattgatt ttcctcanac tcagcctgtg tagctntgaa agcatggaac a gattacact | 300 |
| gcagttnacg tcatcccaca catcttggac tccnagaccc ggggaggtca c atagtccgt | 360 |
| tatgna | 366 |

<210> SEQ ID NO 28
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 28

| | |
|---|---|
| agtgggagcc tcctccttcc ccactcagtt ctttacatcc ccgaggcgca g ctgggcnaa | 60 |
| ggaagtggcc agctgcagcg cctcctgcag gcagccaacg ttcttgcctg t ggcctgtgc | 120 |

```
agacacatcc ttgccaccac ctttaccgtc catcangcct gacacctgct g cacccactc    180 gctngctttt aagccccgat nggctgcatt ctgggggact tgacacaggc n cgtgatctt    240 gccagcctca ttgtccaccg tgaagagcat ggcaaaaagt ctgagggag t gcatcttga    300 anagcttcaa ggcttcattc agggccttng ctnaggcgcc nctctccatc t ccnggaata    360 acnagaggct ggtnngggtn actntcaata aactgcttcg tc                       402
```

<210> SEQ ID NO 29
<211> LENGTH: 175
<212> TYPE: DNA
<213> ORGANISM: Homo sapien

<400> SEQUENCE: 29

```
cggacgggca tgaccggtcc ggtcagctgg gtggccagtt tcagttcttc a gcagaactg    60 tctcccttct tggggccga gggcttcctg gggaagagga tgagtttgga g cggtactcc    120 ttcagccgct gcacgttggt ctgcagggac tccgtggact tgttccgcct c ctcg        175
```

<210> SEQ ID NO 30
<211> LENGTH: 360
<212> TYPE: DNA
<213> ORGANISM: Homo sapien

<400> SEQUENCE: 30

```
ttgtatttct tatgatctct gatgggttct tctcgaaaat gccaagtgga a gactttgtg    60 gcatgctcca gatttaaatc cagctgaggc tccctttgtt ttcagttcca t gtaacaatc    120 tggaaggaaa cttcacggac aggaagactg ctggagaaga gaagcgtgtt a gcccatttg    180 aggtctgggg aatcatgtaa agggtaccca gacctcactt ttagttattt a catcaatga    240 gttctttcag ggaaccaaac ccagaattcg gtgcaaaagc caaacatctt g gtgggattt    300 gataaatgcc ttgggacctg gagtgctggg cttgtgcaca ggaagagcac c agccgctga    360
```

<210> SEQ ID NO 31
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 31

```
acgctctaag cctgtccacg agctcaatag ggaagcctgt gatgactaca g actttgcga    60 acgctacgcc atggtttatg gatacaatgc tgcctataan cgctacttca g gaagcgccg    120 agggaccnaa tgagactgag ggaagaaaaa aaatctcttt ttttctggag g ctggcacct    180 gattttgtat ccccctgtnn cagcattncn gaaatacata ggcttatata c aatgcttct    240 ttcctgtata ttctcttgtc tggctgcacc ccttnttccc gccccagat t gataagtaa    300 tgaaagtgca ctgcagtnag ggtcaaggga gactcancat atgtgattgt t ccntnataa    360 acttctggtg tgatactttc                                                380
```

<210> SEQ ID NO 32
<211> LENGTH: 440
<212> TYPE: DNA
<213> ORGANISM: Homo sapien
<220> FEATURE:
<221> NAME/KEY: misc_feature
<222> LOCATION: (1)...(440)

```
<223> OTHER INFORMATION: n = A,T,C or G

<400> SEQUENCE: 32
gtgtatggga gcccctgact cctcacgtgc ctgatctgtg cccttggtcc c aggtcaggc      60 ccaccccctg cacctccacc tgccccagcc cctgcctctg cccccaagtgg g gccagctgc    120 cctcacttct ggggtggatg atgtgacctt cctngggggga ctgcggaagg g acaagggtt    180 ccctgaagtc ttacggtcca acatcaggac caagtcccat ggacatgctg a cagggtccc    240 caggggagac cgtntcanta gggatgtgtg cctggctgtg tacgtgggtg t gcagtgcac    300 gtganaagca cgtggcggct tctgggggcc atgtttgggg aaggaagtgt g cccnccacc    360 cttggagaac ctcagtcccn gtagcccccct gccctggcac agcngcatnc a cttcaaggg    420 caccctttgg gggttgggt                                                    440

<210> SEQ ID NO 33
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 33
tattttaaca atgtttatta ttcatttatc cctctataga accaccaccc a caccgagga      60 gattatttgg agtgggtccc aacctagggc ctggactctg aaatctaact c cccacttcc    120 ctcattttgt gacttaggtg ggggcatggt tcagtcagaa ctggtgtctc c tattggatc    180 gtgcagaagg aggacctagg cacacacata tggtggccac acccaggagg g ttgattggc    240 aggctggaag acaaaagtct cccaataaag gcacttttac ctcaaagang g ggtgggagt    300 tggtctgctg ggaatgttgt tgttggggtg gggaagantt atttc                      345

<210> SEQ ID NO 34
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 34
tgtaattttt ttattggaaa acaaatatac aacttggaat ggattttgag g caaattgtg      60 ccataagcag attttaagtg gctaaacaaa gtttaaaaag caagtaacaa t aaaagaaaa    120 tgtttctggt acaggaccag cagtacaaaa aaatagtgta cgagtacctg g ataatacac    180 ccgttttgca atagtgcaac ttttaagtac atattgttga ctgtccatag t ccacgcaga    240 gttacaactc cacacttcaa caacaacatg ctgacagttc ctaaagaaaa c tactttaaa    300 aaaggcataa cccagatgtt ccctcatttg accaactcca tctnagttta g atgtgcaga    360 agggcttana ttttcccaga gtaagccnca tgcaacatgt tacttgatca a ttttctaaa    420 ataaggtttt aggacaatga                                                  440

<210> SEQ ID NO 35
<211> LENGTH: 540
<212> TYPE: DNA
<213> ORGANISM: Homo sapien
<220> FEATURE:
<221> NAME/KEY: misc_feature
```

<222> LOCATION: (1)...(540)
<223> OTHER INFORMATION: n = A,T,C or G

<400> SEQUENCE: 35

| | | | | | |
|---|---|---|---|---|---|
| atagatggaa | tttattaagc | ttttcacatg | tgatagcaca | tagttttaat t | gcatccaaa | 60 |
| gtactaacaa | aaactctagc | aatcaagaat | ggcagcatgt | tattttataa c | aatcaacac | 120 |
| ctgtggcttt | taaaatttgg | ttttcataag | ataatttata | ctgaagtaaa t | ctagccatg | 180 |
| cttttaaaaa | atgctttagg | tcactccaag | cttggcagtt | aacatttggc a | taaacaata | 240 |
| ataaacaat | cacaatttaa | taaataacaa | atacaacatt | gtaggccata a | tcatataca | 300 |
| gtataaggga | aaggtggta | gtgttganta | agcagttatt | agaatagaat a | ccttggcct | 360 |
| ctatgcaaat | atgtctagac | actttgattc | actcagccct | gacattcagt t | ttcaaagtt | 420 |
| aggaaacagg | ttctacagta | tcattttaca | gtttccaaca | cattgaaaac a | gtagaaaa | 480 |
| tgatganttg | atttttatta | atgcattaca | tcctcaagan | ttatcaccaa c | ccctcaggt | 540 |

<210> SEQ ID NO 36
<211> LENGTH: 555
<212> TYPE: DNA
<213> ORGANISM: Homo sapien
<220> FEATURE:
<221> NAME/KEY: misc_feature
<222> LOCATION: (1)...(555)
<223> OTHER INFORMATION: n = A,T,C or G

<400> SEQUENCE: 36

| | | | | | |
|---|---|---|---|---|---|
| cttcgtgtgc | ttgaaaattg | agcctgccc | ctcggcccat | aagcccttgt t | gggaactga | 60 |
| gaagtgtata | tggggcccaa | nctactggtg | ccagaacaca | gagacagcag c | ccantgcaa | 120 |
| tgctgtcgag | cattgcaaac | gccatgtgtg | gaactaggag | gaggaatatt c | catcttggc | 180 |
| agaaaccaca | gcattggttt | ttttctactt | gtgtgtctgg | gggaatgaac g | cacagatct | 240 |
| gtttgactt | gttataaaaa | tagggctccc | ccacctcccc | cntttctgtg t | nctttattg | 300 |
| tagcantgct | gtctgcaagg | gagcccctan | ccctggcag | acananctgc t | tcagtgccc | 360 |
| cttcctctc | tgctaaatgg | atgttgatgc | actggaggtc | ttttancctg c | ccttgcatg | 420 |
| gcncctgctg | gaggaagana | aaactctgct | ggcatgaccc | acagtttctt g | actggangc | 480 |
| cntcaaccct | cttggttgaa | gccttgttct | gaccctgaca | tntgcttggg c | nctgggtng | 540 |
| gnctgggctt | ctnaa | | | | | 555 |

<210> SEQ ID NO 37
<211> LENGTH: 280
<212> TYPE: DNA
<213> ORGANISM: Homo sapien
<220> FEATURE:
<221> NAME/KEY: misc_feature
<222> LOCATION: (1)...(280)
<223> OTHER INFORMATION: n = A,T,C or G

<400> SEQUENCE: 37

| | | | | | |
|---|---|---|---|---|---|
| ccaccgacta | taagaactat | gccctcgtgt | attcctgtac | ctgcatcatc c | aactttttc | 60 |
| acgtggattt | tgcttggatc | ttggcaagaa | accctaatct | ccctccagaa a | cagtggact | 120 |
| ctctaaaaaa | tatcctgact | tctaataaca | ttgatntcaa | gaaatgacg g | tcacagacc | 180 |
| aggtgaactg | ccccnagctc | tcgtaaccag | gttctacagg | gaggctgcac c | cactccatg | 240 |
| ttncttctgc | ttcgctttcc | cctaccccac | ccccgccat | | | 280 |

<210> SEQ ID NO 38

<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 38

```
catcgagctg gttgtcttct tgcctgccct gtgtcgtaaa atgggggtcc c ttactgcat       60
tatcaaggga aaggcaagac tgggacgtct agtccacagg aagacctgca c cactgtcgc     120
cttcacacag gtgaactcgg aagacaaagg cgctttggct nagctggtgn a agctatcag    180
gaccaattac aatgacngat acgatnagat ccgccntcac tggggtagca a tgtcctggg     240
tcctaagtct gtggctcgta tcgccnagct cgaanaggcn aangctaaag a acttgccac    300
taa                                                                    303
```

<210> SEQ ID NO 39
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 39

```
gactcagcgg ctggtgctct tcctgtgcac aagcccagca ctccaggtcc c aaggcattt      60
atcaaatccc accaagatnt ttggcttttg caccgaattc tgggtttggt t ccctnaaag    120
aactcattga tgtaaatnac tnaaagtgag gtctgggtac cctttacatg a ttccccaga    180
cctcanatgg gctaacacgc ttctcttctc cagcagtctt cctntccgtg a agttacctt    240
ccagattgtt acatggaact gaanacaaag ggagcctcag ctngatttaa a tctggagca    300
```

<210> SEQ ID NO 40
<211> LENGTH: 318
<212> TYPE: DNA
<213> ORGANISM: Homo sapien
<220> FEATURE:
<221> NAME/KEY: misc_feature
<222> LOCATION: (1)...(318)
<223> OTHER INFORMATION: n = A,T,C or G

<400> SEQUENCE: 40

```
cccaacacaa tggctgagga caaatcagtt ctctgtgacc agacatgaga a ggttgccaa      60
tgggctgttg ggcgaccaag gccttcccgg agtcttcgtc ctctatgagc t ctcgcccat    120
gatggtgaag ctgacggaga agcacaggtc cttcacccac ttcctgacag g tgtgtgcgc    180
catcattggg ggcatgttca cagtggctgg actcatcgat tcgctcatct a ccactcagc    240
acgagccatc cagaaaaaaa ttgatctngg gaagacnacg tagtcaccct c ggtncttcc    300
tctgtctcct ctttctcc                                                    318
```

<210> SEQ ID NO 41
<211> LENGTH: 302
<212> TYPE: DNA
<213> ORGANISM: Homo sapien
<220> FEATURE:
<221> NAME/KEY: misc_feature
<222> LOCATION: (1)...(302)
<223> OTHER INFORMATION: n = A,T,C or G

<400> SEQUENCE: 41

```
acttagatgg ggtccgttca ggggatacca gcgttcacat ttttcctttt a agaaagggt    60 cttggcctga atgttcccca tccggacaca ggctgcatgt ctctgtnagt g tcaaagctg   120 ccatnaccat ctcggtaacc tactcttact ccacaatgtc tatnttcact g cagggctct   180 ataatnagtc cataatgtaa atgcctggcc caagacntat ggcctgagtt t atccnaggc   240 ccaaacnatt accagacatt cctcttanat tgaaaacgga tntctttccc t tggcaaaga   300 tc                                                                   302
```

<210> SEQ ID NO 42
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 42

```
cttaataagt ttaaggccaa ggcccgttcc attcttctag caactgacgt t gccagccga    60 ggtttggaca tacctcatgt aaatgtggtt gtcaactttg acattcctac c cattccaag   120 gattacatcc atcgagtagg tcgaacagct agagctgggc gctccggaaa g gctattact   180 tttgtcacac agtatgatgt ggaactcttc cagcgcatag aacacttnat t gggaagaaa   240 ctaccaggtt ttccaacaca ggatgatgag gttatgatgc tnacggaacg c gtcgctna   299
```

<210> SEQ ID NO 43
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 43

```
ccaacaatgt caagacagcc gtctgtgaca tcccacctcg tggcctcaan a tggcagtca    60 ccttcattgg caatagcaca gccntccggg agctcttcaa gcgcatctcg g agcagttca   120 ctgccatgtt ccgccggaag gccttcctcc actggtacac aggcgagggc a tggacaaga   180 tggagttcac cgaggctgag agcaacatga acgacctcgt ctctnagtat c agcagtacc   240 gggatgccac cgcagaaana ggaggaggat tcggtnagg aggccgaaga a ggaggcctg   300 aggca                                                                305
```

<210> SEQ ID NO 44
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 44

```
tttctgtggg ggaaacctga tctcgacnaa attagagaat tttgtcagcg g tatttcggc    60 tggaacagaa cgaaaacnga tnaatctctg tttcctgtat taaagcaact c gatnrccag   120 cagacacagc tccnaattga ttccttcttt ngattagcac aacagggaga a agaanatgc   180 ttaacgtatt aagagccnga gactaaacag agctttgaca tgtatgctta g gaaagagaa   240
```

```
agaagcagcn gcccgcgnaa ttngaagcng tttctgttgc cntgganaaa g aatttgagc      300 ttctttatta ggccaacgaa aaaccccgaa ananaggcnt tacnataccct t ngaaaantc     360 tccngccnna aaaagaaaga agctttcnga ttcttaacc                              399
```

<210> SEQ ID NO 45
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 45

```
gcgggagcag aagctaaagc caaagcccaa gagagtggca gtgccagcac t ggtgccagt      60 accagtacca ataacagtgc cagtgccagt gccagcacca gtggtggctt c agtgctggt     120 gccagcctga ccgccactct cacatttggg ctcttcgctg gccttggtgg a gctggtgcc    180 agcaccagtg gcagctctgg tgcctgtggt ttctcctaca agtgagattt t aggtatctg    240 ccttggttc agtggggaca tctggggctt anggggcngg ataaggagc t ggatgattc      300 taggaaggcc cangttggag aangatgtgn anagtgtgcc aagacactgc t tttggcatt    360 ttattccttt ctgtttgctg gangtcaatt gacccttnna ntttctctta c ttgtgtttt    420 canatatngt taatcctgcc                                                  440
```

<210> SEQ ID NO 46
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 46

```
gctctgtaat ttcacatttt aaaccttccc ttgacctcac attcctcttc g gccacctct     60 gtttctctgt tcctcttcac agcaaaaact gttcaaaaga gttgttgatt a ctttcattt    120 ccactttctc accccccattc tccctcaat taactctcct tcatcccat g atgccatta    180 tgtggctntt attanagtca ccaaccttat tctccaaaac anaagcaaca a ggactttga    240 cttctcagca gcactcagct ctggtncttg aaacacccccc gttacttgct a ttcctccta   300 cctcataaca atctccttcc cagcctctac tgctgccttc tctgagttct t cccagggtc    360 ctaggctcag atgtagtgta gctcaaccct gctacacaaa gnaatctcct g aaagcctgt    420 aaaaatgtcc atncntgtcc tgtgagtgat ctnccangna naataacaaa t t            472
```

<210> SEQ ID NO 47
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 47

```
ccttcctccg cctggccatc cccagcatgc tcatgctgtg catggagtgg t gggcctatg     60 aggtcgggag cttcctcagt ggtctgtatg aggatggat acgggactg g tggaacct      120 gggggccctg tctgggtgca aggcgacagc tgtctttctt caccaggcat c ctcggcatg    180
```

```
gtggagctgg gcgctcagtc catcgtgtat gaactggcca tcattgtgta c atggtccct    240 gcaggcttca gtgtggctgc cagtgtccgg gtangaaacg ctctgggtgc t ggagacatg    300 gaagcaggca cggaagtcct ctaccgtttc cctgctgatt acagtgctct t tgctgtanc    360 cttcagtgtc ctgctgttaa gctgtaagga tcacntgggg tacatttttta c taccgaccg   420 agaacatcat taatctggtg gctcaggtgg ttccaattta tgctgtttcc c acctctttg    480 aagctcttgc tgctcaggta cacgccaatt ttgaaaagta acaacgtgc c tcggagtgg    540 gaattctgct                                                            550

<210> SEQ ID NO 48
<211> LENGTH: 214
<212> TYPE: DNA
<213> ORGANISM: Homo sapien
<220> FEATURE:
<221> NAME/KEY: misc_feature
<222> LOCATION: (1)...(214)
<223> OTHER INFORMATION: n = A,T,C or G

<400> SEQUENCE: 48
agaaggacat aaacaagctg aacctgccca agacgtgtga tatcagcttc t cagatccag    60 acaacctcct caacttcaag ctggtcatct gtcctgatna gggcttctac n agagtggga   120 agtttgtgtt cagttttaag gtgggccagg gttacccgca tgatcccccc a aggtgaagt   180 gtgagacnat ggtctatcac cccnacattg acct                                 214

<210> SEQ ID NO 49
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 49
atctgcctaa aatttattca aataatgaaa atnaatctgt tttaagaaat t cagtctttt    60 agtttttagg acaactatgc acaaatgtac gatggagaat tcttttttgga t naactctag  120 gtngaggaac ttaatccaac cggagctntt gtgaaggtca gaanacagga g agggaatct   180 tggcaaggaa tggagacnga gtttgcaaat tgcagctaga gtnaatngtt n taaatggga   240 ctgctnttgt gtctcccang gaaagtt                                         267

<210> SEQ ID NO 50
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 50
gactgggtca agctgcatg aaaccaggcc ctggcagcaa cctgggaatg g ctggaggtg    60 ggagagaacc tgacttctct ttccctctcc ctcctccaac attactggaa c tctgtcctg   120 ttgggatctt ctgagcttgt ttccctgctg ggtgggacag aggacaaagg a gagggagg   180 gtctagaaga ggcagcccctt ctttgtcctc tggggtnaat gagcttgacc t anagtagat  240 ggagagacca anagcctctg atttttaatt tccataanat gttcnaagta t atntntacc  300
```

<210> SEQ ID NO 51
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 51

| | | |
|---|---|---|
| gggtaaaatc ctgcagcacc cactctggaa atactgctc ttaattttcc t gaaggtggc | 60 |
| cccctatttc tagttggtcc aggattaggg atgtggggta tagggcattt a aatcctctc | 120 |
| aagcgctctc caagcacccc cggcctgggg gtnagtttct catcccgcta c tgctgctgg | 180 |
| gatcaggttn aataaatgga actcttcctg tctggcctcc aaagcagcct a aaaactgag | 240 |
| gggctctgtt agagggacc tccaccctnn ggaagtccga ggggctnggg a agggtttct | 300 |

<210> SEQ ID NO 52
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 52

| | | |
|---|---|---|
| aaaatcaact tcntgcatta atanacanat tctanancag gaagtgaana t aatttctg | 60 |
| cacctatcaa ggaacnnact tgattgcctc tattnaacan atatatcgag t tnctatact | 120 |
| tacctgaata ccnccgcata actctcaacc nanatncntc nccatgacac t cnttcttna | 180 |
| atgctantcc cgaattcttc attatatcng tgatgttcgn cctgntnata t atcagcaag | 240 |
| gtatgtnccn taactgccga nncaang | 267 |

<210> SEQ ID NO 53
<211> LENGTH: 401
<212> TYPE: DNA
<213> ORGANISM: Homo sapien

<400> SEQUENCE: 53

| | | |
|---|---|---|
| agsctttagc atcatgtaga agcaaactgc acctatggct gagataggtg c aatgaccta | 60 |
| caagattttg tgttttctag ctgtccagga aaagccatct tcagtcttgc t gacagtcaa | 120 |
| agagcaagtg aaaccatttc cagcctaaac tacataaaag cagccgaacc a atgattaaa | 180 |
| gacctctaag gctccataat catcattaaa tatgcccaaa ctcattgtga c tttttattt | 240 |
| tatatacagg attaaaatca acattaaatc atcttattta catggccatc g gtgctgaaa | 300 |
| ttgagcattt taaatagtac agtaggctgg tatacattag gaaatggact g cactggagg | 360 |
| caaatagaaa actaaagaaa ttagataggc tggaaatgct t | 401 |

<210> SEQ ID NO 54
<211> LENGTH: 401
<212> TYPE: DNA
<213> ORGANISM: Homo sapien

<400> SEQUENCE: 54

| | | |
|---|---|---|
| cccaacacaa tggataaaaa cacttatagt aaatggggac attcactata a tgatctaag | 60 |
| aagctacaga ttgtcatagt tgttttcctg ctttacaaaa ttgctccaga t ctggaatgc | 120 |
| cagtttgacc tttgtcttct ataatatttc ctttttttcc cctctttgaa t ctctgtata | 180 |

```
tttgattctt aactaaaatt gttctcttaa atattctgaa tcctggtaat t aaaagtttg    240 ggtgtatttt ctttacctcc aaggaaagaa ctactagcta caaaaaatat t ttggaataa    300 gcattgtttt ggtataaggt acatattttg gttgaagaca ccagactgaa g taaacagct    360 gtgcatccaa tttattatag ttttgtaagt aacaatatgt a                         401

<210> SEQ ID NO 55
<211> LENGTH: 933
<212> TYPE: DNA
<213> ORGANISM: Homo sapien

<400> SEQUENCE: 55
tttactgctt ggcaaagtac cctgagcatc agcagagatg ccgagatgaa a tcagggaac     60 tcctagggga tgggtcttct attacctggg aacacctgag ccagatgcct t acaccacga   120 tgtgcatcaa ggaatgcctc cgcctctacg caccggtagt aaactatccc g gttactcga   180 caaacccatc acctttccag atggacgctc cttacctgca ggaataactg t gtttatcaa   240 tatttgggct cttcaccaca acccctattt ctgggaagac cctcaggtct t taaccccctt   300 gagattctcc agggaaaatt ctgaaaaaat acatccctat gccttcatac c attctcagc   360 tggattaagg aactgcattg ggcagcattt tgccataatt gagtgtaaag t ggcagtggc   420 attaactctg ctccgcttca agctggctcc agaccactca aggccaccca g ctgtcgtca   480 agttgcctca gtccaagaa tggaatccat gtgtttgcaa aaaaagtttg c taattttaa   540 gtccttttcg tataagaatt aakgagacaa ttttcctacc aaaggaagaa c aaaaggata   600 aatataatac aaaatatatg tatatggttg tttgacaaat tatataactt a ggatacttc   660 tgactggttt tgacatccat taacagtaat tttaatttct ttgctgtatc t ggtgaaacc   720 cacaaaaaca cctgaaaaaa ctcaagctga gttccaatgc gaagggaaat g attggtttg   780 ggtaactagt ggtagagtgg ctttcaagca tagtttgatc aaaactccac t cagtatctg   840 cattactttt atctctgcaa atatctgcat gatagcttta ttctcagtta t ctttcccca   900 taataaaaaa tatctgccaa aaaaaaaaaa aaa                                  933

<210> SEQ ID NO 56
<211> LENGTH: 480
<212> TYPE: DNA
<213> ORGANISM: Homo sapien

<400> SEQUENCE: 56
ggctttgaag cattttttgtc tgtgctccct gatcttcagg tcaccaccat g aagttctta    60 gcagtcctgg tactcttggg agtttccatc tttctggtct ctgcccagaa t ccgacaaca   120 gctgctccag ctgacacgta tccagctact ggtcctgctg atgatgaagc c cctgatgct   180 gaaaccactg ctgctgcaac cactgcgacc actgctgctc ctaccactgc a accaccgct   240 gcttctacca ctgctcgtaa agacattcca gttttaccca atgggttggg g atctcccg   300 aatggtagag tgtgtccctg agatggaatc agcttgagtc ttctgcaatt g gtcacaact   360 attcatgctt cctgtgattt catccaacta cttaccttgc ctacgatatc c cctttatct   420 ctaatcagtt tattttcttt caaataaaaa ataactatga gcaacaaaaa a aaaaaaaa   480

<210> SEQ ID NO 57
<211> LENGTH: 798
<212> TYPE: DNA
<213> ORGANISM: Homo sapien
```

-continued

```
<400> SEQUENCE: 57
agcctacctg gaaagccaac cagtcctcat aatggacaag atccaccagc t cctcctgtg      60 gactaacttt gtgatatggg aagtgaaaat agttaacacc ttgcacgacc a aacgaacga     120 agatgaccag agtactctta accccttaga actgtttttc cttttgtatc t gcaatatgg    180 gatggtattg ttttcatgag cttctagaaa tttcacttgc aagtttattt t tgcttcctg    240 tgttactgcc attcctattt acagtatatt tgagtgaatg attatatttt t aaaaagtta    300 catgggctt ttttggttgt cctaaactta caaacattcc actcattctg t ttgtaactg     360 tgattataat ttttgtgata atttctggcc tgattgaagg aaatttgaga g gtctgcatt    420 tatatatttt aaatagattt gataggtttt taaattgctt tttttcataa g gtatttata    480 aagttatttg gggttgtctg ggattgtgtg aaagaaaatt agaaccccgc t gtatttaca    540 tttaccttgg tagtttattt gtggatggca gttttctgta gttttgggga c tgtggtagc    600 tcttggattg ttttgcaaat tacagctgaa atctgtgtca tggattaaac t ggcttatgt    660 ggctagaata ggaagagaga aaaatgaaa tggttgttta ctaattttat a ctcccatta     720 aaaattttta atgttaagaa aaccttaaat aaacatgatt gatcaatatg g aaaaaaaa     780 aaaaaaaaaa aaaaaaaa                                                    798

<210> SEQ ID NO 58
<211> LENGTH: 280
<212> TYPE: DNA
<213> ORGANISM: Homo sapien

<400> SEQUENCE: 58
ggggcagctc ctgaccctcc acagccacct ggtcagccac cagctggggc a acgagggtg     60 gaggtcccac tgagcctctc gcctgccccc gccactcgtc tggtgcttgt t gatccaagt    120 cccctgcctg gtcccccaca aggactccca tccaggcccc ctctgccctg c cccttgtca   180 tggaccatgg tcgtgaggaa gggctcatgc cccttattta tgggaaccat t tcattctaa   240 cagaataaac cgagaaggaa accagaaaaa aaaaaaaaa                            280

<210> SEQ ID NO 59
<211> LENGTH: 382
<212> TYPE: DNA
<213> ORGANISM: Homo sapien

<400> SEQUENCE: 59
aggcgggagc agaagctaaa gccaaagccc aagagagtgg cagtgccagc a ctggtgcca     60 gtaccagtac caataacagt gccagtgcca gtgccagcac cagtggtggc t tcagtgctg    120 gtgccagcct gaccgccact ctcacatttg ggctcttcgc tggccttggt g gagctggtg    180 ccagcaccag tggcagctct ggtgcctgtg gtttctccta caagtgagat t ttagatatt   240 gttaatcctg ccagtctttc tcttcaagcc agggtgcatc ctcagaaacc t actcaacac    300 agcactctag gcagccacta tcaatcaatt gaagttgaca ctctgcatta a atctatttg    360 ccattaaaaa aaaaaaaaaa aa                                                382

<210> SEQ ID NO 60
<211> LENGTH: 602
<212> TYPE: DNA
<213> ORGANISM: Homo sapien

<400> SEQUENCE: 60
tgaagagccg cgcggtggag ctgctgcccg atgggactgc caaccttgcc a agctgcagc     60
```

-continued

```
ttgtggtgga gaatagtgcc cagcgggtca tccacttggc gggtcagtgg g agaagcacc      120 gggtcccatc ctcgtgagta ccgccactcc gaaagctgca ggattgcaga g agctggaat     180 cttctcgacg gctggcagag atccaagaac tgcaccagag tgtccgggcg g ctgctgaag    240 aggcccgcag gaaggaggag gtctataagc agctgatgtc agagctggag a ctctgccca     300 gagatgtgtc ccggctggcc tacacccagc gcatcctgga gatcgtgggc a acatccgga    360 agcagaagga agagatcacc aagatcttgt ctgatacgaa ggagcttcag a aggaaatca    420 actccctatc tgggaagctg gaccggacgt tgcggtgac tgatgagctt g tgttcaagg     480 atgccaagaa ggacgatgct gttcggaagg cctataagta tctagctgct c tgcacgaga    540 actgcagcca gctcatccag accatcgagg acacaggcac catcatgcgg g aggttcgag    600 ac                                                                     602
```

<210> SEQ ID NO 61
<211> LENGTH: 1368
<212> TYPE: DNA
<213> ORGANISM: Homo sapien
<220> FEATURE:
<221> NAME/KEY: misc_feature
<222> LOCATION: (1)...(1368)
<223> OTHER INFORMATION: n = A,T,C or G

<400> SEQUENCE: 61

```
ccagtgagcg cgcgtaatac gactcactat agggcgaatt gggtaccggg c cccccctcg      60 agcggccgcc ctttttttt tttttttatt gatcagaatt caggctttat t attgagcaa    120 tgaaaacagc taaaacttaa ttccaagcat gtgtagttaa agtttgcaaa g tgggatatt    180 gttcacaaaa cacattcaat gtttaaacac tatttatttg aagaacaaaa t atatttaaa    240 attgtttgct tctaaaaagc ccatttccct ccaagtctaa actttgtaat t tgatattaa    300 gcaatgaagt tattttgtac aatctagtta aacaagcaga atagcactag g cagaataaa    360 aaattgcaca gacgtatgca attttccaag atagcattct ttaaattcag t tttcagctt    420 ccaaagattg gttgcccata atagacttaa acatataatg atggctaaaa a aaataagta    480 tacgaaaatg taaaaaagga aatgtaagtc cactctcaat ctcataaaag g tgagagtaa    540 ggatgctaaa gcaaataaa tgtaggttct ttttttctgt ttccgtttat c atgcaatct    600 gcttctttga tatgccttag ggttacccat ttaagttaga ggttgtaatg c aatggtggg    660 aatgaaaatt gatcaaatat acaccttgtc atttcatttc aaattgcggg c tggaaactt    720 ccaaaaaaag ggtaggcatg aagaaaaaaa aaatcmaatc agaacctctt c aggggtttg    780 kgktctgata tggcagacar gatacaagtc ccaccaggag atggagcaat t caaaataag    840 ggtaatgggc tgacaaggta ttattgccag catgggacag aatgagcaac a ggctgaaaa    900 gttttttggat tatatagcac ctagagtctc tgatgtaggg aattttttgtt a gtcaaacat    960 acgctaaact tccaagggaa aatctttcag gtagcctaag cttgcttttc t agagtgatg   1020 agttgcattg ctactgtgat ttttttgaaaa caaactgggt ttgtacaagt g agaaagact  1080 agagagaaag attttagtct gtttagcaga agccatttta tctgcgtgca c atggatcaa   1140 tatttctgat ccctatacc ccaggaaggg caaaatccca agaaatgtg t tagcaaaat   1200 tggctgatgc tatcatattg ctatggacat tgatcttgcc caacacaatg g aattccacc  1260 acactggact agtggatcca ctagttctag agcggccggc caccgcgtg g agctccagc   1320 ttttgttccc tttagtgagg gttaattgcg cgcttggcgt aatcatnn              1368
```

<210> SEQ ID NO 62
<211> LENGTH: 924
<212> TYPE: DNA
<213> ORGANISM: Homo sapien
<220> FEATURE:
<221> NAME/KEY: misc_feature
<222> LOCATION: (1)...(924)
<223> OTHER INFORMATION: n = A,T,C or G

<400> SEQUENCE: 62

| | | | | | |
|---|---|---|---|---|---|
| caaaggnaca | ggaacagctt | gnaaagtact | gncatnoctn | cctgcaggga c | cagcccttt 60 |
| gcctccaaaa | gcaataggaa | atttaaaaga | tttncactga | gaaggggncc a | cgtttnart 120 |
| tntnaatgtn | tcargnanar | tnccttncaa | atgncrnctn | cactnactnr g | natttgggt 180 |
| tnccgnrtnc | mgnactatnt | caggtttgaa | aaactggatc | tgccacttat c | agttatgtg 240 |
| accttaaaga | actccgttaa | tttctcagag | cctcagtttc | cttgtctata a | gttgggagt 300 |
| aatattaata | ctatcatttt | tccaaggatt | gatgtgaaca | ttaatgaggt g | aaatgacag 360 |
| atgtgtatca | tggttcctaa | taaacatcca | aaatatagta | cttactattg t | cattattat 420 |
| tacttgtttg | aagctaaaga | cctcacaata | gaatcccatc | cagcccacca g | acagagytc 480 |
| tgagttttct | agtttggaag | agctattaaa | taacaacktc | tagtgtcaat t | ctatacttg 540 |
| ttatggtcaa | gtaactgggc | tcagcatttt | acattcattg | tctctttaag t | tctagcaat 600 |
| gtgaagcagg | aactatgatt | atattgacta | cataaatgaa | gaaattgagg c | tcagataca 660 |
| ttaagtaatt | ctcccagggt | cacacagcta | gaactggcaa | agcctgggat t | gatccatga 720 |
| tcttccagca | ttgaagaatc | ataaatgtaa | ataactgcaa | ggccttttcc t | cagaagagc 780 |
| tcctggtgct | tgcaccaacc | cactagcact | tgttctctac | aggggaacat c | tgtgggcct 840 |
| gggaatcact | gcacgtcgca | agagatgttg | cttctgatga | attattgttc c | tgtcagtgg 900 |
| tgtgaaggca | aaaaaaaaaa | aaaa | | | 924 |

<210> SEQ ID NO 63
<211> LENGTH: 1079
<212> TYPE: DNA
<213> ORGANISM: Homo sapien

<400> SEQUENCE: 63

| | | | | | |
|---|---|---|---|---|---|
| agtcccaaga | actcaataat | ctcttatgtt | ttcttttgaa | gacttatttt a | aatattaac 60 |
| tatttcggtg | cctgaatgga | aaaatataaa | cattagctca | gagacaatgg g | gtacctgtt 120 |
| tggaatccag | ctggcagcta | taagcaccgt | tgaaaactct | gacaggcttt g | tgcccttt 180 |
| tattaaatgg | cctcacatcc | tgaatgcagg | aatgtgttcg | tttaaataaa c | attaatctt 240 |
| taatgttgaa | ttctgaaaac | acaaccataa | atcatagttg | gtttttctgt g | acaatgatc 300 |
| tagtacatta | tttcctccac | agcaaaccta | cctttccaga | aggtggaaat t | gtatttgca 360 |
| acaatcaggg | caaacccac | acttgaaaag | cattttacaa | tattatatct a | agttgcaca 420 |
| gaagacccca | gtgatcacta | ggaaatctac | cacagtccag | ttttttctaat c | caagaaggt 480 |
| caaacttcgg | ggaataatgt | gtccctcttc | tgctgctgct | ctgaaaaata t | tcgatcaaa 540 |
| acgaagttta | caagcagcag | ttattccaag | attagagttc | atttgtgtat c | ccatgtata 600 |
| ctggcaatgt | ttaggtttgc | ccaaaaactc | ccagacatcc | acaatgttgt t | gggtaaacc 660 |
| accacatctg | gtaacctctc | gatccctag | atttgtatct | cctgcaaata t | aactgtagc 720 |
| tgactctgga | gcctcttgca | ttttctttaa | aaccatttt | aactgattca t | tcgttccgc 780 |
| agcatgccct | ctggtgctct | ccaaatggga | tgtcataagg | caaagctcat t | tcctgacac 840 |

```
attcacatgc acacataaaa ggtttctcat cattttggta cttggaaaag g aataatctc      900 ttggctttttt aatttcactc ttgatttctt caacattata gctgtgaaat a tccttcttc     960 atgacctgta ataatctcat aattacttga tctcttcttt aggtagctat a atatgggg      1020 aataacttcc tgtagaaata tcacatctgg gctgtacaaa gctaagtagg a acacaccc      1079
```

<210> SEQ ID NO 64
<211> LENGTH: 1001
<212> TYPE: DNA
<213> ORGANISM: Homo sapien

<400> SEQUENCE: 64

```
gaatgtgcaa cgatcaagtc agggtatctg tggtatccac cactttgagc a tttatcgat      60 tctatatgtc aggaacattt caagttatct gttctagcaa ggaaatataa a atacttata    120 gttaactatg gcctatctac agtgcaacta aaaactagat tttattcctt t ccacctgtg    180 ggtttgtatt catttaccac cctcttttca ttcccttttct cacccacaca c tgtgccggg    240 cctcaggcat atactattct actgtctgtc tctgtaagga ttatcatttt a gcttccaca    300 tatgagagaa tgcatgcaaa gttttttcttt ccatgtctgg cttatttcac t taacataat    360 gacctccgct tccatccatg ttattttatat tacccaatag tgttcataaa t atatataca    420 cacatatata ccacattgca tttgtccaat tattcattga cggaaactgg t taatgttat    480 atcgttgcta ttgtggatag tgctgcaata aacacgcaag tggggatata a tttgaagag    540 ttttttttgtt gatgttcctc caaattttaa gattgttttg tctatgtttg t gaaatggc    600 gttagtattt tcatagagat tgcattgaat ctgtagattg ctttgggtaa g tatggttat    660 tttgatggta ttaattttttt cattccatga agatgagatg tctttccatt g tttgtgtcc    720 tctacatttt ctttcatcaa gttttgttg tatttttgaa gtagatgtat t tcaccttat    780 agatcaagtg tattccctaa atattttatt tttgtagcta ttgtagatga a attgccttc    840 ttgatttctt tttcacttaa ttcattatta gtgtatggaa atgttatgga t ttttatttg    900 ttggtttttta atcaaaaact gtattaaact tagagttttt tgtggagttt t taagttttt    960 ctagatataa gatcatgaca tctaccaaaa aaaaaaaaaa a                         1001
```

<210> SEQ ID NO 65
<211> LENGTH: 575
<212> TYPE: DNA
<213> ORGANISM: Homo sapien

<400> SEQUENCE: 65

```
acttgatata aaaaggatat ccataatgaa tattttatac tgcatccttt a cattagcca      60 ctaaatacgt tattgcttga tgaagacctt tcacagaatc ctatggattg c agcatttca    120 cttggctact tcatacccat gccttaaaga ggggcagttt ctcaaaagca g aaacatgcc    180 gccagttctc aagttttcct cctaactcca tttgaatgta agggcagctg g cccccaatg    240 tggggaggtc cgaacatttt ctgaattccc attttcttgt tcgcggctaa a tgacagttt    300 ctgtcattac ttagattccc gatctttccc aaaggtgttg atttacaaag a ggccagcta    360 atagccagaa atcatgaccc tgaaagagag atgaaatttc aagctgtgag c caggcagga    420 gctccagtat ggcaaaggtt cttgagaatc agccatttgg tacaaaaaag a ttttttaaag    480 ctttttatgtt ataccatgga gccatagaaa ggctatggat tgtttaagaa c tatttttaaa    540 gtgttccaga cccaaaaagg aaaaaaaaaa aaaaa                                  575
```

<210> SEQ ID NO 66
<211> LENGTH: 831
<212> TYPE: DNA
<213> ORGANISM: Homo sapien

<400> SEQUENCE: 66

```
attgggctcc ttctgctaaa cagccacatt gaaatggttt aaaagcaagt c agatcaggt        60
gatttgtaaa attgtatta tctgtacatg tatgggcttt taattcccac c aagaaagag       120
agaaattatc tttttagtta aaaccaaatt tcacttttca aatatcttc c aacttattt       180
attggttgtc actcaattgc ctatatatat atatatatat gtgtgtgtgt g tgtgtgcgc       240
gtgagcgcac gtgtgtgtat gcgtgcgcat gtgtgtgtat gtgtattatc a gacataggt       300
ttctaacttt tagatagaag aggagcaaca tctatgccaa atactgtgca t tctacaatg       360
gtgctaatct cagacctaaa tgatactcca tttaattaa aaaagagttt t aataatta        420
tctatgtgcc tgtatttccc ttttgagtgc tgcacaacat gttaacatat t agtgtaaaa       480
gcagatgaaa caaccacgtg ttctaaagtc tagggattgt gctataatcc c tatttagtt       540
caaaattaac cagaattctt ccatgtgaaa tggaccaaac tcatattatt g ttatgtaaa       600
tacagagttt taatgcagta tgacatccca caggggaaaa gaatgtctgt a gtgggtgac       660
tgttatcaaa tattttatag aatacaatga acggtgaaca gactggtaac t tgtttgagt       720
tcccatgaca gatttgagac ttgtcaatag caaatcattt ttgtatttaa a ttttgtac        780
tgatttgaaa aacatcatta aatatcttta aaagtaaaaa aaaaaaaaa a                 831
```

<210> SEQ ID NO 67
<211> LENGTH: 590
<212> TYPE: DNA
<213> ORGANISM: Homo sapien

<400> SEQUENCE: 67

```
gtgctctgtg tattttttta ctgcattaga cattgaatag taatttgcgt t aagatacgc        60
ttaaaggctc tttgtgacca tgtttccctt tgtagcaata aaatgttttt t acgaaaact       120
ttctccctgg attagcagtt taaatgaaac agagttcatc aatgaaatga g tatttaaaa       180
taaaaatttg ccttaatgta tcagttcagc tcacaagtat tttaagatga t tgagaagac       240
ttgaattaaa gaaaaaaaaa ttctcaatca tattttaaa atataagact a aaattgttt       300
ttaaaacaca tttcaaatag aagtgagttt gaactgacct tatttatact c ttttaagt         360
ttgttccttt tccctgtgcc tgtgtcaaat cttcaagtct tgctgaaaat a catttgata       420
caaagttttc tgtagttgtg ttagttcttt tgtcatgtct gtttttggct g aagaaccaa       480
gaagcagact tttctttaa aagaattatt tctctttcaa atatttctat c ctttttaaa       540
aaattccttt ttatggctta tatacctaca tatttaaaaa aaaaaaaaa                   590
```

<210> SEQ ID NO 68
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 68

```
gttccctttt ccggtcggcg tggtcttgcg agtggagtgt ccgctgtgcc c gggcctgca        60
ccatgagcgt cccggccttc atcgacatca gtgaagaaga tcaggctgct g agcttcgtg       120
```

```
cttatctgaa atctaaagga gctgagattt cagaagagaa ctcggaaggt g gacttcatg      180 ttgatttagc tcaaattatt gaagcctgtg atgtgtgtct gaaggaggat g ataaagatg      240 ttgaaagtgt gatgaacagt ggggnatcct actcttgatc cggaanccna c                291

<210> SEQ ID NO 69
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 69
tctatgagca tgccaaggct ctgtgggagg atgaaggagt gcgtgcctgc t acgaacgct      60 ccaacgagta ccagctgatt gactgtgccc agtacttcct ggacaagatc g acgtgatca     120 agcaggctga ctatgtgccg agcgatcagg acctgcttcg ctgccgtgtc c tgacttctg     180 gaatctttga gaccaagttc caggtggacn aagtcaactt ccacatgntt g acgtgggtg    240 gccagcgcga tgaacgccgc aagtggatcc agtgcttcaa cgatgtgact g ccatcatct     300 t                                                                       301

<210> SEQ ID NO 70
<211> LENGTH: 201
<212> TYPE: DNA
<213> ORGANISM: Homo sapien

<400> SEQUENCE: 70
gcggctcttc ctcgggcagc ggaagcggcg cggcggtcgg agaagtggcc t aaaacttcg     60 gcgttgggtg aaagaaaatg ccccgaacca agcagactgc tcgtaagtcc a ccggtggga    120 aagccccccg caaacagctg gccacgaaag ccgccaggaa aagcgctccc t ctaccggcg    180 gggtgaagaa gcctcatcgc t                                                 201

<210> SEQ ID NO 71
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 71
gccggggtag tcgccgncgc cgccgccgct gcagccactg caggcaccgc t gccgccgcc    60 tgagtagtgg gcttaggaag gaagaggtca tctcgctcgg agcttcgctc g gaagggtct    120 ttgttccctg cagccctccc acgggaatga caatggataa aagtgagctg g tacanaaag    180 ccaaactcgc tgagcaggct gagcgatatg atgatatggc tgcagccatg a aggcagtca    240 cagaacaggg gcatgaactc ttcaacgaag agagaaatct gctctctggt g cctacaaga    300 a                                                                       301

<210> SEQ ID NO 72
<211> LENGTH: 251
<212> TYPE: DNA
<213> ORGANISM: Homo sapien
<220> FEATURE:
<221> NAME/KEY: misc_feature
<222> LOCATION: (1)...(251)
```

<223> OTHER INFORMATION: n = A,T,C or G

<400> SEQUENCE: 72

| cttgggggt | gttggggag | agactgtggg | cctggaaata | aaacttgtct | c ctctaccac | 60 |
| cacctgtac | cctagcctgc | acctgtccac | atctctgcaa | agttcagctt | c cttccccag | 120 |
| gtctctgtgc | actctgtctt | ggatgctctg | gggagctcat | gggtggagga | g tctccacca | 180 |
| gagggaggct | cagggactg | gttgggccag | ggatgaatat | ttgagggata | a aaattgtgt | 240 |
| aagagccaan | g | | | | | 251 |

<210> SEQ ID NO 73
<211> LENGTH: 895
<212> TYPE: DNA
<213> ORGANISM: Homo sapien

<400> SEQUENCE: 73

| tttttttttt | ttttcccag | gccctctttt | tatttacagt | gataccaaac | c atccacttg | 60 |
| caaattcttt | ggtctcccat | cagctggaat | taagtaggta | ctgtgtatct | t tgagatcat | 120 |
| gtatttgtct | ccactttggt | ggatacaaga | aaggaaggca | cgaacagctg | a aaaagaagg | 180 |
| gtatcacacc | gctccagctg | gaatccagca | ggaacctctg | agcatgccac | a gctgaacac | 240 |
| ttaaaagagg | aaagaaggac | agctgctctt | catttatttt | gaaagcaaat | t catttgaaa | 300 |
| gtgcataaat | ggtcatcata | agtcaaacgt | atcaattaga | ccttcaacct | a ggaaacaaa | 360 |
| attttttttt | tctatttaat | aatacaccac | actgaaatta | tttgccaatg | a atcccaaag | 420 |
| atttggtaca | aatagtacaa | ttcgtatttg | ctttcctctt | tcctttcttc | a gacaaacac | 480 |
| caaataaaat | gcaggtgaaa | gagatgaacc | acgactagag | gctgacttag | a aatttatgc | 540 |
| tgactcgatc | taaaaaaaat | tatgttggtt | aatgttaatc | tatctaaaat | a gagcatttt | 600 |
| gggaatgctt | ttcaaagaag | gtcaagtaac | agtcatacag | ctagaaaagt | c cctgaaaaa | 660 |
| aagaattgtt | aagaagtata | ataacctttt | caaaacccac | aatgcagctt | a gttttcctt | 720 |
| tatttatttg | tggtcatgaa | gactatcccc | atttctccat | aaaatcctcc | c tccatactg | 780 |
| ctgcattatg | gcacaaaaga | ctctaagtgc | caccagacag | aaggaccaga | g tttctgatt | 840 |
| ataaacaatg | atgctgggta | atgtttaaat | gagaacattg | gatatggatg | g tcag | 895 |

<210> SEQ ID NO 74
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 74

| tgtgcncagg | ggatgggtgg | gcngtggaga | ngatgacaga | aaggctggaa | g gaanggggg | 60 |
| tgggtttgaa | ggccanggcc | aagggncct | caggtccgnt | tctgnnaagg | g acagccttg | 120 |
| aggaaggagn | catggcaagc | catagctagg | ccaccaatca | gattaagaaa | n nctgagaaa | 180 |
| nctagctgac | catcactgtt | ggtgnccagt | ttcccaacac | aatggaatnc | c accacactg | 240 |
| gactagngga | nccactagtt | ctagagcggc | cgccaccgcg | gtggaacccc | a acttttgcc | 300 |
| cctttagnga | gggttaattg | cgcgcttggc | ntaatcatgg | tcataagctg | t | 351 |

<210> SEQ ID NO 75
<211> LENGTH: 251

```
<212> TYPE: DNA
<213> ORGANISM: Homo sapien

<400> SEQUENCE: 75
tacttgacct  tctttgaaaa  gcattcccaa  aatgctctat  tttagataga  t taacattaa      60 ccaacataat  tttttttaga  tcgagtcagc  ataaatttct  aagtcagcct  c tagtcgtgg     120 ttcatctctt  tcacctgcat  tttatttggt  gtttgtctga  agaaaggaaa  g aggaaagca     180 aatacgaatt  gtactatttg  taccaaatct  ttgggattca  ttggcaaata  a tttcagtgt     240 ggtgtattat  t                                                                 251

<210> SEQ ID NO 76
<211> LENGTH: 251
<212> TYPE: DNA
<213> ORGANISM: Homo sapien

<400> SEQUENCE: 76
tatttaataa  tacaccacac  tgaaattatt  tgccaatgaa  tcccaaagat  t tggtacaaa      60 tagtacaatt  cgtatttgct  ttcctctttc  ctttcttcag  acaaacacca  a ataaaatgc     120 aggtgaaaga  gatgaaccac  gactagaggc  tgacttagaa  atttatgctg  a ctcgatcta     180 aaaaaaatta  tgttggttaa  tgttaatcta  tctaaaatag  agcattttgg  g aatgctttt     240 caaagaaggt  c                                                                 251

<210> SEQ ID NO 77
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 77
actcaccgtg  ctgtgtgctg  tgtgcctgct  gcctggcagc  ctggccctgc  c gctgctcag      60 gaggcgggag  gcatgagtga  gctacagtgg  gaacaggctc  aggactatct  c aagagannn     120 tatctctatg  actcagaaac  aaaaaatgcc  aacagtttag  aagccaaact  c aaggagatg     180 caaaaattct  ttggcctacc  tataactgga  atgttaaact  cccgcgtcat  a gaaataatg     240 cagaagccca  gatgtggagt  gccagatgtt  gcagaatact  cactatttcc  a aatagccca     300 aaatggactt  ccaaagtggt  cacctacagg  atcgtatcat  atactcgaga  c                351

<210> SEQ ID NO 78
<211> LENGTH: 1574
<212> TYPE: DNA
<213> ORGANISM: Homo sapien

<400> SEQUENCE: 78
gccctggggg  cggagqggag  gggcccacca  cggccttatt  tccgcgagcg  c cggcactgc      60 ccgctccgag  cccgtgtctg  tcgggtgccg  agccaacttt  cctgcgtcca  t gcagcccg     120 ccggcaacgg  ctgcccgctc  cctggtccgg  gcccaggggc  ccgcgcccca  c cgccccgct     180 gctcgcgctg  ctgctgttgc  tcgccccggt  ggcggcgccc  gcggggtccg  g gaccccga     240 cgaccctggg  cagcctcagg  atgctggggt  cccgcgcagg  ctcctgcagc  a ggcggcgcg     300 cgcggcgctt  cacttcttca  acttccggtc  cggctcgccc  agcgcgctgc  g agtgctggc     360 cgaggtgcag  gagggccgcg  cgtggattaa  tccaaaagag  ggatgtaaag  t tcacgtggt     420
```

-continued

```
cttcagcaca gagcgctaca acccagagtc tttacttcag gaaggtgagg g acgtttggg      480 gaaatgttct gctcgagtgt ttttcaagaa tcagaaaccc agaccaacta t caatgtaac      540 ttgtacacgg ctcatcgaga aaagaaaag acaacaagag gattacctgc t ttacaagca       600 aatgaagcaa ctgaaaaacc ccttggaaat agtcagcata cctgataatc a tggacatat      660 tgatccctct ctgagactca tctgggattt ggctttcctt ggaagctctt a cgtgatgtg      720 ggaaatgaca acacaggtgt cacactacta cttggcacag ctcactagtg t gaggcagtg     780 gaaaactaat gatgatacaa ttgattttga ttatactgtt ctacttcatg a attatcaac     840 acaggaaata attccctgtc gcattcactt ggtctggtac cctggcaaac c tcttaaagt     900 gaagtaccac tgtcaagagc tacagacacc agaagaagcc tccggaactg a agaaggatc    960 agctgtagta ccaacagagc ttagtaattt ctaaaaagaa aaaatgatct t tttccgact    1020 tctaaacaag tgactatact agcataaatc attcttctag taaaacagct a aggtataga   1080 cattctaata atttgggaaa acctatgatt acaagtaaaa actcagaaat g caaagatgt   1140 tggtttttttg tttctcagtc tgctttagct tttaactctg gaagcgcatg c acactgaac  1200 tctgctcagt gctaaacagt caccagcagg ttcctcaggg tttcagccct a aaatgtaaa   1260 acctggataa tcagtgtatg ttgcaccaga atcagcattt tttttttaac t gcaaaaaat   1320 gatggtctca tctctgaatt tatatttctc attcttttga acatactata g ctaatatat   1380 tttatgttgc taaattgctt ctatctagca tgttaaacaa agataatata c tttcgatga   1440 aagtaaatta taggaaaaaa attaactgtt ttaaaaagaa cttgattatg t tttatgatt    1500 tcaggcaagt attcattttt aacttgctac ctacttttaa ataaatgttt a catttctaa   1560 aaaaaaaaaa aaaa                                                      1574

<210> SEQ ID NO 79
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 79
catactgtga attgttcttg actccttttc ttgacattca gttttcanaa t ttccatctt     60 tcttctggaa ctaatgtgct gttctcttga ctgcctgctg ggccagcatc c gattgccag    120 ccagaaacgt cacactgccc aagatggcca ggtacttcaa ggtctggaac a tgttgagct    180 gagtccagta gacatacatg agtcccagca tagcagcatg tcccaggtga a atataatcg    240 tgctaggagc aaaagtgaag ttggagacat tggcaccaat ccggatccac t agttctaga   300 gcggccgcca ccgcggtgga gctccagctt tgttcccctt tagtgagggt t aattgcgcg   360 cttggcgtaa tcatggncat agctgttttcc tgtgtgaaat t                        401

<210> SEQ ID NO 80
<211> LENGTH: 301
<212> TYPE: DNA
<213> ORGANISM: Homo sapien

<400> SEQUENCE: 80
aaaaatgaaa catctatttt agcagcaaga ggctgtgagg gatggggtag a aaaggcatc    60 ctgagagagt tctagaccga cccaggtcct gtggcacact atacgggtca g gaggggtgg   120 aagacaggcc taagctctag gacggtgaat ctcggggcta tttgtggatt t gttagaaac   180
```

```
agacattctt ttggccttt  cctggcactg gtgttgccgg caggtgggca g aagtgagcc      240 accagtcact gttcagtcat tgccaccaca gatcttcagc agaatcttcc g gtaatcccc      300 t                                                                      301

<210> SEQ ID NO 81
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 81
tagccaggtt gctcaagcta attttattct ttcccaacag gatccatttg g aaaatatca      60 agcctttaga atgtggcagc aagagaaagc ggactacgca ggaacgggga g tttgggaga     120 agctctcctg gtgttgactt agggatgaag gctccaggct gctgccagaa a tggagtcac    180 cagcagaaga actgntttct ctgataagga tgtcccacca ttttcaagct g ttcgttaaa    240 gttacacagg tccttcttgc agcagtaagt accgttagct cattttccct c aagcgggtt    300 t                                                                      301

<210> SEQ ID NO 82
<211> LENGTH: 201
<212> TYPE: DNA
<213> ORGANISM: Homo sapien
<220> FEATURE:
<221> NAME/KEY: misc_feature
<222> LOCATION: (1)...(201)
<223> OTHER INFORMATION: n = A,T,C or G

<400> SEQUENCE: 82
tcaacagaca aaaaagtttt attgaataca aaactcaaag gcatcaacag t cctgggccc      60 aagagatcca tggcaggaag tcaagagttc tgcttcaggg tcggtctggg c agccctgga    120 agaagtcatt gcacatgaca gtgatgagtg ccaggaaaac agcatactcc t ggaaagtcc    180 acctgctggn cactgnttca t                                                201

<210> SEQ ID NO 83
<211> LENGTH: 251
<212> TYPE: DNA
<213> ORGANISM: Homo sapien
<220> FEATURE:
<221> NAME/KEY: misc_feature
<222> LOCATION: (1)...(251)
<223> OTHER INFORMATION: n = A,T,C or G

<400> SEQUENCE: 83
gtaaggagca tactgtgccc atttattata gaatgcagtt aaaaaaaata t tttgaggtt      60 agcctctcca gttttaaaagc acttaacaag aaacacttgg acagcgatgc a atggtctct   120 cccaaaccgg ctccctctta ccaagtaccg taaacagggt tgagaacgt t caatcaatt    180 tcttgatatg aacaatcaaa gcatttaatg caaacatatt tgcttctcaa a naataaaac    240 cattttccaa a                                                           251

<210> SEQ ID NO 84
<211> LENGTH: 301
<212> TYPE: DNA
<213> ORGANISM: Homo sapien
<220> FEATURE:
```

```
<221> NAME/KEY: misc_feature
<222> LOCATION: (1)...(301)
<223> OTHER INFORMATION: n = A,T,C or G

<400> SEQUENCE: 84
agtttataat gttttactat gatttagggc ttttttttca aagaacaaaa a ttataagca      60 taaaaactca ggtatcagaa agactcaaaa ggctgttttt cactttgttc a gattttgtt    120 tccaggcatt aagtgtgtca tacagttgtt gccactgctg ttttccaaat g tccgatgtg    180 tgctatgact gacaactact tttctctggg tctgatcaat tttgcagtan a ccattttag    240 ttcttacggc gtcnataaca aatgcttcaa catcatcagc tccaatctga a gtcttgctg    300 c                                                                     301

<210> SEQ ID NO 85
<211> LENGTH: 201
<212> TYPE: DNA
<213> ORGANISM: Homo sapien

<400> SEQUENCE: 85
tatttgtgta tgtaacattt attgacatct acccactgca agtatagatg a ataagacac     60 agtcacacca taaggagtt tatccttaaa aggagtgaaa gacattcaaa a accaactgc    120 aataaaaaag ggtgacataa ttgctaaatg gagtggagga acagtgctta t caattcttg   180 attgggccac aatgatatac c                                              201

<210> SEQ ID NO 86
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 86
tttataaaat attttattta cagtagagct ttacaaaaat agtcttaaat t aatacaaat     60 cccttttgca atataactta tatgactatc ttctcaaaaa cgtgacattc g attataaca   120 cataaactac atttatagtt gttaagtcac cttgtatgtat aaatatgttt t catctttt    180 tttgtaataa ggtacatacc aataacaatg aacaatggac aacaaatctt a ttttgntat   240 tcttccaatg taaaattcat ctctggccaa aacaaaatta accaagaaa a gtaaaacaa    300 t                                                                     301

<210> SEQ ID NO 87
<211> LENGTH: 351
<212> TYPE: DNA
<213> ORGANISM: Homo sapien
<220> FEATURE:
<221> NAME/KEY: misc_feature
<222> LOCATION: (1)...(351)
<223> OTHER INFORMATION: n = A,T,C or G

<400> SEQUENCE: 87
aaaaaagatt taagatcata aataggtcat tgttgtcaca acacatttca g aatcttaaa     60 aaaacaaaca ttttggcttt ctaagaaaaa gacttttaaa aaaaatcaat t ccctcatca   120 ctgaaaggac ttgtacattt ttaaacttcc agtctcctaa ggcacagtat t taatcagaa   180 tgccaatatt accaccctgc tgtagcanga ataaagaagc aagggattaa c acttaaaaa   240 aacngccaaa ttcctgaacc aaatcattgg cattttaaaa aagggataaa a aaacnggnt   300
```

```
aagggggga gcattttaag taaagaaggg ccaagggtgg tatgccngga c          351
```

<210> SEQ ID NO 88
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 88

```
gttttaggtc tttaccaatt tgattggttt atcaacaggg catgaggttt a aatatatct    60
ttgaggaaag gtaaagtcaa atttgacttc ataggtcatc ggcgtcctca c tcctgtgca   120
ttttctggtg gaagcacaca gttaattaac tcaagtgtgg cgntagcgat g cttttcat    180
ggngtcattt atccacttgg tgaacttgca cacttgaatg naaactcctg g gtcattggg   240
ntggccgcaa gggaaaggtc cccaagacac caaaccttgc agggtacctn t gcacaccaa   300
c                                                                    301
```

<210> SEQ ID NO 89
<211> LENGTH: 591
<212> TYPE: DNA
<213> ORGANISM: Homo sapien

<400> SEQUENCE: 89

```
tttttttttt tttttttatt aatcaaatga ttcaaaacaa ccatcattct g tcaatgccc    60
aagcacccag ctggtcctct ccccacatgt cacactctcc tcagcctctc c cccaaccct   120
gctctccctc ctcccctgcc ctagcccagg acagagtct aggaggagcc t ggggcagag   180
ctggaggcag gaagagagca ctggacagac agctatggtt tggattgggg a agagattag   240
gaagtaggtt cttaaagacc cttttttagt accagatatc cagccatatt c ccagctcca   300
ttattcaaat catttcccat agcccagctc ctctctgttc tccccctact a ccaattctt   360
tggctcttac acaattttta tccctcaaat attcatccct ggcccaacca g tcccctgag   420
cctccctctg gtggagactc ctccacccat gagctccca gagcatccaa g acagagtgc   480
acagagacct ggggaaggaa gctgaacttt gcagagatgt ggacaggtgc a ggctagggt   540
acagggtggt ggtagaggag acaagttta tttccaggcc cacagtctct c         591
```

<210> SEQ ID NO 90
<211> LENGTH: 1978
<212> TYPE: DNA
<213> ORGANISM: Homo sapien

<400> SEQUENCE: 90

```
tttttttttt tttttatca aatgaatact ttattagaga cataacacgt a taaataaa     60
ttctttca tcatggagtt accagatttt aaaccaacc aacactttct c atttttaca    120
gctaagacat gttaaattct taaatgccat aattttgtt caactgcttt g tcattcaac   180
tcacaagtct agaatgtgat taagctacaa atctaagtat tcacagatgt g tcttaggct   240
tggtttgtaa caatctagaa gcaatctgtt tacaaaagtg ccaccaaagc a ttttaaaga   300
aaccaattta atgccaccaa acataagcct gctatacctg ggaaacaaaa a atctcacac   360
ctaaattcta gcagagtaaa cgattccaac tagaatgtac tgtatatcca t atggcacat   420
ttatgactt gtaatatgta attcataata caggtttagg tgtgtggtat g gagctagga   480
```

-continued

```
aaaccaaagt agtaggatat tatagaaaag atctgatgtt aagtataaag t catatgcct    540 gatttcctca aacctttttgt ttttcctcat gtcttctgtc tttatatttt t atcacaaac   600 caagatctaa cagggttctt tctagaggat tattagataa gtaacacttg a tcattaagc    660 acggatcatg ccactcattc atggttgttc tatgttccat gaactctaat a gcccaactt   720 atacatggca ctccaagggg atgcttcagc cagaaagtaa agggctgaaa a agtagaaca    780 atacaaaagc cctcgtgtgg tgggaactgt ggcctcactc ttacttgtcc t tccattcaa   840 aacagtttgg cacctttcca tgacgaggat ctctacaggt aggttaaaat a cttttctgt   900 gctattcagc cagaaatagt ttttgtgctg gatatgattt taaaacagat t ttgtctgtc   960 accagtgcaa aaacattaca gatgtctggg ctaatacaaa aacacataag a atctacaac  1020 tttatattta atactctatt caaatttaac tcaaagtaat gcaaaataat t agaagtaaa  1080 aacttaattc ttctgagagc tctatttgga aaagcttcac atatccacac a caaatatgg  1140 gtatattcat gcacagggca acaactgta ttctgaagca taaataaact c aaagtaaga  1200 catcagtagc tagataccag ttccagtatt ggttaatggt ctctggggat c ccattttaa  1260 gcactctcag atgaggatct tgctcagttg ttagactatc attagtttga t taagcaact  1320 gaagtttact tcataaatta cttttttccta tatccaggac tctgcctgag a aattttata  1380 cattcctcca aaggtaagta ttctccaaag gtaagtatttt gactattaac a caaaggcaa  1440 tgtgattatt gcataatgac actaaatatt atgtggcttt tctgttaggt t tataagttt  1500 tcaatgatca gttcaagaaa atgcagatca tatataacta aggttttaca c cagtggttg  1560 acaaactatg gcccacaggc taaacccagc ctccccttgt ttttataaat a gttttatt   1620 agacataacc acactcattc atttctgtat tgtgtatagc tgctttcacg c tatactagc  1680 agaactgaat agttgtgaca gagactgtat ggaccgtgaa gcataaatat t taccatctg  1740 gcccattcta aaaaaagtgt gccaattcct ggtttacact aaaatataga g tttagtggg  1800 aagcctattt gaaatgtgtt tttttttaggg gctgtaatta ccaattaaaa t taaggttca  1860 ggtgactcag caaccaaaca aaagggatac taatttttta tgaacaatat a tttgtattt  1920 tatggacata aaaggaaact ttcagaaaga aaaggaggaa aataaagggg g aaaggga    1978
```

<210> SEQ ID NO 91
<211> LENGTH: 895
<212> TYPE: DNA
<213> ORGANISM: Homo sapien

<400> SEQUENCE: 91

```
tttttttttt tttttttcttg tttaaaaaaa ttgttttcat tttaatgatc t gagttagta   60 acaaacaaat gtacaaaatt gtctttcaca tttccataca ttgtgttatg g accaaatga   120 aaacgctgga ctcaaatgc aggtttcttt atatccttaa cttcaattat t gtcacttat   180 aaataaaggt gatttgctaa cacatgcatt tgtgaacaca gatgccaaaa a ttatacatg   240 taagttaatg cacaaccaag agtatacact gttcatttgt gcagttatgc g tcaaatgcg   300 actgacacag aagcagttat cctgggatat ttcactctat atgaaaagca t cttggagaa   360 atagattgaa atacagttta aaacaaaaat tgtattctac aaatacaata a aatttgcaa   420 cttgcacatc tgaagcaaca tttgagaaag ctgcttcaat aaccctgctg t tatattggt   480 tttataggta tatctccaaa gtcatgggtt gggatatagc tgctttaaag a aaataaata   540 tgtatattaa aaggaaaatc acactttaaa aatgtgagga aagctttgaa a acagtctta   600 atgcatgagt ccatctacat attttcaagt tttggaaaca gaaagaagtt t agaattttc   660
```

-continued

```
aaagtaatct gaaaactttc taagccattt taaaataaga ttttttttccc c atctttcca    720 atgtttccta tttgatagtg taatacagaa atgggcagtt tctagtgtca a cttaactgt    780 gctaattcat aagtcattat acatttatga cttaagagtt caaataagtg g aaattgggt    840 tataatgaaa atgacaaggg ggcccccttca gcagccactc atctgaacta g taat        895

<210> SEQ ID NO 92
<211> LENGTH: 1692
<212> TYPE: DNA
<213> ORGANISM: Homo sapien

<400> SEQUENCE: 92
tttttttttt tttttaactt ttagcagtgt ttattttttgt taaaagaaac c aattgaatt    60 gaaggtcaag acaccttctg attgcacaga ttaaacaaga aagtattact t atttcaact   120 ttacaaagca tcttattgat ttaaaaagat ccatactatt gataaagttc a ccatgaaca   180 tatatgtaat aaggagacta aaatattcat tttacatatc tacaacatgt a tttcatatt   240 tctaatcaac cacaaatcat ataggaaaat atttaggtcc atgaaaaagt t tcaaaacat   300 taaaaaatta aagttttgaa acaaatcaca tgtgaaagct cattaaataa t aacattgac   360 aaataaatag ttaatcagct ttacttatta gctgctgcca tgcatttctg g cattccatt   420 ccaagcgagg gtcagcatgc agggtataat ttcatactat gcgaccgtaa a gagctacag   480 ggcttatttt tgaagtgaaa tgtcacaggg tctttcattc tctttcaaag g aagatcact   540 catggctgct aaactgttcc catgaagagt accaaaaaag cacctttctg a aatgttact   600 gtgaagattc atgacaacat atttttttta acctgttttg aaggagtttt g tttaggaga   660 ggggatgggc cagtagatgg agggtatctg agaagcccctt ttctgttttta a aatataatg   720 attcactgat gtttatagta tcaacagtct tttaagaaca atgaggaatt a aaactacag   780 gatacgtgga atttaaatgc aaattgcatt catggatata cctacatctt g aaaaacttg   840 aaaaggaaaa actattccca agaaggtcc tgatacttaa acagcttgc t gggtttgat   900 caaagcagaa agcatatact ttcaagtgag aaaacagcag tggcaggctt g agtcttcca   960 agcaatcaaa tctgtaaagc agatggttac tagtaagtct agttatggga g tctgagttc  1020 taactcatgc tgtgcttgct ggatttgctg gctcttttcc gctctctgtg a tgctggact  1080 ggcttgtcag gtgacatgct ctcaaagttg tgactggact cgttgtgctg c cgggtgtac  1140 ctcttgcact tgcaggcagt gactactgtg attttgtagg tgcgtgtgct g ccatcttgg  1200 cactgcagct ggattctctg ggtacgggtt ttgtcattga cacaccgcca c tcctgggag  1260 ctcctcctgc tccagtactt tgttccatag cctcctccaa tccagttagg g agcactggc  1320 agggggcaagc actcgccagc acacaccagc tccttcagag ggctgatgct g gtgcactgg  1380 ccatcagaga tgtatttggt ggaacgcagt tcccggcaac ccacttgaac c cgagtgttc  1440 cgatccagtc cagtgttact gaaatgcctg cctccatttc tggcttgatt c aacgtgctg  1500 ttgctgctgg ggtgtgctgg aacaggttta accacatgtg aataaaggat t tctgtggca  1560 tcattttttaa aagccaaaca gcttttcatt aggatgcatg caagggaag g agatagaaa  1620 tgaatggcag gaggaagcat ggtgagtaga ggatttgctt gactgaagag c tggttaatt  1680 cttttgcctc tg                                                      1692

<210> SEQ ID NO 93
<211> LENGTH: 251
<212> TYPE: DNA
```

<213> ORGANISM: Homo sapien

<400> SEQUENCE: 93

| | | | | | |
|---|---|---|---|---|---|
| cccaccctac | ccaaatatta | gacaccaaca | cagaaaagct | agcaatggat t | cccttctac   60 |
| tttgttaaat | aaataagtta | aatatttaaa | tgcctgtgtc | tctgtgatgg c | aacagaagg  120 |
| accaacaggc | cacatcctga | taaaggtaa | gagggggtg | gatcagcaaa a | agacagtgc  180 |
| tgtgggctga | ggggacctgg | ttcttgtgtg | ttgcccctca | agactcttcc c | ctacaaata  240 |
| actttcatat | g | | | |            251 |

<210> SEQ ID NO 94
<211> LENGTH: 735
<212> TYPE: DNA
<213> ORGANISM: Homo sapien

<400> SEQUENCE: 94

| | | | | | |
|---|---|---|---|---|---|
| tttttttttt | ttttccact | tctcagttta | tttctgggac | taaatttggg t | cagagctgc   60 |
| agagaaggga | tgggccctga | gcttgaggat | gaaagtgccc | cagggagatt g | agacgcaac  120 |
| ccccgccctg | gacagttttg | gaaattgttc | ccagggttca | actagagaga c | acggtcagc  180 |
| ccaatgtggg | ggaagcagac | cctgagtcca | ggagacatgg | ggtcagggc t | ggagagatg  240 |
| aacattctca | acatctctgg | gaaggaatga | gggtctgaaa | ggagtgtcag g | gctgtccct  300 |
| gcagcaggtg | gggatgccgg | tgtgctgagt | cctgggatga | ctcaggagtt g | gcctggatg  360 |
| gtttcctgga | tccacttggt | gaacttgcag | aggttcgtgt | agacacccgg t | ctgttgggc  420 |
| cgggcacaag | ggtaatctcc | ccaggacacg | agtccctgca | gggagccatt g | cagaccaca  480 |
| ggccccccag | aatcaccctg | gcaggagtct | ctacctgctt | tgtcaccggc g | cagaacatg  540 |
| gtgtcatcta | tctgtctcgg | gtaagcatcc | tcgcaccttt | tctgacttag c | acgctgata  600 |
| ttcaagcact | ggaggacctt | agggaagtgc | acttgggggc | tcttggttgt c | cccagcca  660 |
| gacaccaagc | actttgtccc | agcagaggga | caatgagagg | agacgttgat g | ggtctgaca  720 |
| tctttagtgg | gacga | | | |            735 |

<210> SEQ ID NO 95
<211> LENGTH: 578
<212> TYPE: DNA
<213> ORGANISM: Homo sapien

<400> SEQUENCE: 95

| | | | | | |
|---|---|---|---|---|---|
| cttgccttct | cttaggctttt | gaagcattttt | tgtctgtgct | ccctgatctt c | aggtcacca   60 |
| ccatgaagtt | cttagcagtc | ctggtactct | tgggagtttc | catctttctg g | tctctgccc  120 |
| agaatccgac | aacagctgct | ccagctgaca | cgtatccagc | tactggtcct g | ctgatgatg  180 |
| aagcccctga | tgctgaaacc | actgctgctg | caaccactgc | gaccactgct g | ctcctacca  240 |
| ctgcaaccac | cgctgcttct | accactgctc | gtaaagacat | tccagtttta c | ccaaatggg  300 |
| ttggggatct | cccgaatggt | agagtgtgtc | cctgagatgg | aatcagcttg a | gtcttctgc  360 |
| aattggtcac | aactattcat | gcttcctgtg | atttcatcca | actacttacc t | tgcctacga  420 |
| tatccccttt | atctctaatc | agtttatttt | ctttcaaata | aaaataact a | tgagcaaca  480 |
| aaaaaaaaa | aaaaaaaaa | aaaaaaaaa | aaaaaaaaa | aaaaaaaaa a | aaaaaaaa  540 |
| aaaaaaaaa | aaaaaaaaa | aaaaaaaaa | aaaaaaa | |            578 |

<210> SEQ ID NO 96
<211> LENGTH: 594

<212> TYPE: DNA
<213> ORGANISM: Homo sapien

<400> SEQUENCE: 96

| | | | | | |
|---|---|---|---|---|---|
| atggcaaaga | atggacttgt | aatttgcatc | ctggtgatca | ccttactcct g | gaccagacc | 60 |
| accagccaca | catccagatt | aaaagccagg | aagcacagca | aacgtcgagt g | agagacaag | 120 |
| gatggagatc | tgaagactca | aattgaaaag | ctctggacag | aagtcaatgc c | ttgaaggaa | 180 |
| attcaagccc | tgcagacagt | ctgtctccga | ggcactaaag | ttcacaagaa a | tgctacctt | 240 |
| gcttcagaag | gtttgaagca | tttccatgag | gccaatgaag | actgcatttc c | aaaggagga | 300 |
| atcctggtta | tccccaggaa | ctccgacgaa | atcaacgccc | tccaagacta t | ggtaaaagg | 360 |
| agcctgccag | gtgtcaatga | cttttggctg | gcatcaatg | acatggtcac g | aaggcaag | 420 |
| tttgttgacg | tcaacggaat | cgctatctcc | ttcctcaact | gggaccgtgc a | cagcctaac | 480 |
| ggtggcaagc | gagaaaactg | tgtcctgttc | tcccaatcag | ctcagggcaa g | tggagtgat | 540 |
| gaggcctgtc | gcagcagcaa | gagatacata | tgcgagttca | ccatccctca a | tag | 594 |

<210> SEQ ID NO 97
<211> LENGTH: 3101
<212> TYPE: DNA
<213> ORGANISM: Homo sapien

<400> SEQUENCE: 97

| | | | | | |
|---|---|---|---|---|---|
| tgttggggcc | tcagcctccc | aagtagctgg | gactacaggt | gcctgccacc a | cgcccagct | 60 |
| aattttttgt | atattttta | gtagagacgg | ggtttcaccg | tggtctcaat c | tcctgacct | 120 |
| cgtgatctgc | cagccttggc | ctcccaaagt | gtattctctt | tttattatta t | tattatttt | 180 |
| tgagatggag | tctgtctctg | tcgcccaggc | tggagtgcag | tggtgcgatc t | ctgctcact | 240 |
| gcaagctccg | cctcctgggt | tcatgccatt | ctcctgcctc | agcctcccga g | tagctggga | 300 |
| ctacaggccc | tgccaccac | acccggctaa | ttttttgtat | ttttagtaga g | acagggttt | 360 |
| caccatgtta | gccagggtgg | tctctatctt | ctgacctcgt | gatccgcctg c | ctcagtctc | 420 |
| tcaaagtgct | gggattacag | gcgtgagcca | ccgcgaccag | ccaactattg c | tgtttattt | 480 |
| ttaaatatat | tttaaagaaa | caattagatt | tgttttcttt | ctcattcttt t | acttctact | 540 |
| cttcatgtat | gtataattat | atttgtgttt | tctattacct | tttctccttt t | actgtattg | 600 |
| gactataata | attgtgctca | ctaatttctg | ttcactaata | ttatcagctt a | gataatact | 660 |
| ttaattttta | acttatatat | tgagtattaa | attgatcagt | tttatttgta a | ttatctatc | 720 |
| ttccgcttgg | ctgaatataa | cttcttaagc | ttataacttc | ttgttctttc c | atgttattt | 780 |
| ttttctttt | tttaatgtat | tgaatttctt | ctgacactca | ttctagtaac t | tttttctcg | 840 |
| gtgtgcaacg | taagttataa | tttgtttctc | agatttgaga | tctgccataa g | tttgaggct | 900 |
| ttatttttt | tttttatttg | ctttatggca | agtcggacaa | cctgcatgga t | ttggcatca | 960 |
| atgtagtcac | ccatatctaa | gagcagcact | tgcttcttag | catgatgagt t | gtttctgga | 1020 |
| ttgttctttt | attttactta | tattcctggt | agattcttat | attttccctt c | aactctatt | 1080 |
| cagcatttta | ggaattctta | ggactttctg | agaattttag | ctttctgtat t | aaatgtttt | 1140 |
| taatgagtat | tgcattttct | caaaaagcac | aaatatcaat | agtgtacaca t | gaggaaaac | 1200 |
| tatatatata | ttctgttgca | gatgacagca | tctcataaca | aaatcctagt t | acttcattt | 1260 |
| aaaagacagc | tctcctccaa | tatactatga | ggtaacaaaa | atttgtagtg t | gtaattttt | 1320 |
| ttaatattag | aaaactcatc | ttacattgtg | cacaaatttc | tgaagtgata a | tacttcact | 1380 |

```
gtttttctat agaagtaact taatattggc aaaattactt atttgaattt a ggttttggc    1440
tttcatcata tacttcctca ttaacatttc cctcaatcca taaatgcaat c tcagtttga    1500
atcttccatt taacccagaa gttaattttt aaaaccttaa taaaatttga a tgtagctag    1560
atattatttg ttggttacat attagtcaat aatttatatt acttacaatg a tcagaaaat    1620
atgatctgaa tttctgctgt cataaattca ataacgtatt ttaggcctaa a cctttccat    1680
ttcaaatcct tgggtctggt aattgaaaat aatcattatc ttttgttttc t ggccaaaaa    1740
tgctgcccat ttatttctat ccctaattag tcaaactttc taataaatgt a tttaacgtt    1800
aatgatgttt atttgcttgt tgtatactaa aaccattagt ttctataatt t aaatgtcac    1860
ctaatatgag tgaaaatgtg tcagaggctg gggaagaatg tggatggaga a agggaaggt    1920
gttgatcaaa aagtacccaa gtttcagtta cacaggaggc atgagattga t ctagtgcaa    1980
aaaatgatga gtaaataaaa taataatgca ctgtatattt tgaaattgct a aaagtagat    2040
ttaaaattga tttacataat attttacata tttataaagc acatgcaata t gttgttaca    2100
tgtatagaat gtgcaacgat caagtcaggg tatctgtggt atccaccact t tgagcattt    2160
atcgattcta tatgtcagga acatttcaag ttatctgttc tagcaaggaa a tataaaata    2220
cattatagtt aactatggcc tatctacagt gcaactaaac actagattt a ttcctttcc    2280
aactgtgggt ttgtattcat ttaccaccct cttttcattc cctttctcac c cacacactg    2340
tgccgggcct caggcatata ctattctact gtctgtctct gtaaggatta t cattttagc    2400
ttccacatat gagagaatgc atgcaaagtt tttctttcca tgtctggctt a tttcactta    2460
acaaaatgac ctccgcttcc atccatgtta tttatattac ccaatagtgt t cataaatat    2520
atatacacac atatatacca cattgcattt gtccaattat tcattgacgg a aactggtta    2580
atgttatatc gttgctattg tgaatagtgc tgcaataaac acgcaagtgg g gatataatt    2640
tgaagagttt ttttgttgat gttccataca aattttaaga ttgttttgtc t atgtttgtg    2700
aaaatggcgt tagtattttc atagagattg cattgaatct gtagattgct t tgggtaagt    2760
atggttattt tgatggtatt aattttttca ttccatgaag atgagatgtc t ttccatttg    2820
tttgtgtcct ctacattttc tttcatcaaa gttttgttgt atttttgaag t agatgtatt    2880
tcaccttata gatcaagtgt attccctaaa tattttattt ttgtagctat t gtagatgaa    2940
attgccttct cgatttcttt ttcacttaat tcattattag tgtatggaaa t gttatggat    3000
ttttatttgt tggttttaa tcaaaaactg tattaaactt agagtttttt g tggagtttt    3060
taagttttc tagatataag atcatgacat ctaccaaaaa a                          3101
```

<210> SEQ ID NO 98
<211> LENGTH: 90
<212> TYPE: PRT
<213> ORGANISM: Homo sapien

<400> SEQUENCE: 98

Met Lys Phe Leu Ala Val Leu Val Leu Gly Val Ser Ile Phe Leu
1               5                   10                  15

Val Ser Ala Gln Asn Pro Thr Thr Ala Ala Pro Ala Asp Thr Tyr Pro
            20                  25                  30

Ala Thr Gly Pro Ala Asp Asp Glu Ala Pro Ala Glu Thr Thr Ala
        35                  40                  45

Ala Ala Thr Thr Ala Thr Thr Ala Ala Pro Thr Thr Ala Thr Thr Ala
    50                  55                  60

Ala Ser Thr Thr Ala Arg Lys Asp Ile Pro Val Leu Pro Lys Trp Val

-continued

```
                65                  70                  75                  80
        Gly Asp Leu Pro Asn Gly Arg Val Cys Pro
                            85                  90

<210> SEQ ID NO 99
<211> LENGTH: 197
<212> TYPE: PRT
<213> ORGANISM: Homo sapien

<400> SEQUENCE: 99

Met Ala Lys Asn Gly Leu Val Ile Cys Ile L eu Val Ile Thr Leu Leu
 1               5                  10                  15

Leu Asp Gln Thr Thr Ser His Thr Ser Arg L eu Lys Ala Arg Lys His
                20                  25                  30

Ser Lys Arg Arg Val Arg Asp Lys Asp Gly A sp Leu Lys Thr Gln Ile
            35                  40                  45

Glu Lys Leu Trp Thr Glu Val Asn Ala Leu L ys Glu Ile Gln Ala Leu
        50                  55                  60

Gln Thr Val Cys Leu Arg Gly Thr Lys Val H is Lys Lys Cys Tyr Leu
65                  70                  75                  80

Ala Ser Glu Gly Leu Lys His Phe His Glu A la Asn Glu Asp Cys Ile
                85                  90                  95

Ser Lys Gly Gly Ile Leu Val Ile Pro Arg A sn Ser Asp Glu Ile Asn
            100                 105                 110

Ala Leu Gln Asp Tyr Gly Lys Arg Ser Leu P ro Gly Val Asn Asp Phe
        115                 120                 125

Trp Leu Gly Ile Asn Asp Met Val Thr Glu G ly Lys Phe Val Asp Val
    130                 135                 140

Asn Gly Ile Ala Ile Ser Phe Leu Asn Trp A sp Arg Ala Gln Pro Asn
145                 150                 155                 160

Gly Gly Lys Arg Glu Asn Cys Val Leu Phe S er Gln Ser Ala Gln Gly
                165                 170                 175

Lys Trp Ser Asp Glu Ala Cys Arg Ser Ser L ys Arg Tyr Ile Cys Glu
            180                 185                 190

Phe Thr Ile Pro Gln
        195

<210> SEQ ID NO 100
<211> LENGTH: 3410
<212> TYPE: DNA
<213> ORGANISM: Homo sapien

<400> SEQUENCE: 100
gggaaccagc ctgcacgcgc tggctccggg tgacagccgc gcgcctcggc c aggatctga      60 gtgatgagac gtgtccccac tgaggtgccc cacagcagca ggtgttgagc a tgggctgag    120 aagctggacc ggcaccaaag ggctggcaga aatgggcgcc tggctgattc c taggcagtt    180 ggcggcagca aggaggagag gccgcagctt ctggagcaga gccgagacga a gcagttctg    240 gagtgcctga acggccccct gagccctacc cgcctggccc actatggtcc a gaggctgtg    300 ggtgagccgc ctgctgcggc accggaaagc ccagctcttg ctggtcaacc t gctaacctt    360 tggcctggag gtgtgtttgg ccgcaggcat cacctatgtg ccgcctctgc t gctggaagt    420 gggggtagag gagaagttca tgaccatggt gctgggcatt ggtccagtgc t gggcctggt    480 ctgtgtcccg ctcctaggct cagccagtga ccactggcgt ggacgctatg g ccgccgccg    540 gcccttcatc tgggcactgt ccttgggcat cctgctgagc ctctttctca t cccaagggc    600
```

```
cggctggcta gcagggctgc tgtgcccgga tcccaggccc ctggagctgg c actgctcat    660 cctgggcgtg gggctgctgg acttctgtgg ccaggtgtgc ttcactccac t ggaggccct    720 gctctctgac ctcttccggg acccggacca ctgtcgccag gcctactctg t ctatgcctt    780 catgatcagt cttgggggct gcctgggcta cctcctgcct gccattgact g ggacaccag    840 tgccctggcc cctacctgg gcacccagga ggagtgcctc tttggcctgc t caccctcat     900 cttcctcacc tgcgtagcag ccacactgct ggtggctgag gaggcagcgc t gggccccac    960 cgagccagca gaagggctgt cggcccctc cttgtcgccc cactgctgtc c atgccgggc    1020 ccgcttggct ttccggaacc tgggcgccct gcttccccgg ctgcaccagc t gtgctgccg    1080 catgccccgc accctgcgcc ggctcttcgt ggctgagctg tgcagctgga t ggcactcat    1140 gaccttcacg ctgttttaca cggatttcgt gggcgagggg ctgtaccagg g cgtgcccag    1200 agctgagccg ggcaccgagg cccggagaca ctatgatgaa ggcgttcgga t gggcagcct    1260 ggggctgttc ctgcagtgcg ccatctccct ggtcttctct ctggtcatgg a ccggctggt    1320 gcagcgattc ggcactcgag cagtctattt ggccagtgtg gcagctttcc c tgtggctgc    1380 cggtgccaca tgcctgtccc acagtgtggc cgtggtgaca gcttcagccg c cctcaccgg    1440 gttcaccttc tcagccctgc agatcctgcc ctacacactg gcctccctct a ccaccggga    1500 gaagcaggtg ttcctgccca ataccgagg ggacactgga ggtgctagca g tgaggacag    1560 cctgatgacc agcttcctgc caggcccctaa gctggagct cccttcccta a tggacacgt    1620 gggtgctgga ggcagtggcc tgctcccacc tccacccgcg ctctgcgggg c ctctgcctg    1680 tgatgtctcc gtacgtgtgg tggtgggtga gcccaccgag gccagggtgg t tccgggccg    1740 gggcatctgc ctggacctcg ccatcctgga tagtgccttc ctgctgtccc a ggtggcccc    1800 atccctgttt atgggctcca ttgtccagct cagccagtct gtcactgcct a tatggtgtc    1860 tgccgcaggc ctgggtctgg tcgccattta ctttgctaca caggtagtat t tgacaagag    1920 cgacttggcc aaaatactcag cgtagaaaac ttccagcaca ttgggtgga g ggcctgcct    1980 cactgggtcc cagctccccg ctcctgttag ccccatgggg ctgccgggct g gccgccagt    2040 ttctgttgct gccaaagtaa tgtggctctc tgctgccacc ctgtgctgct g aggtgcgta    2100 gctgcacagc tggggctgg ggcgtccctc tcctctctcc ccagtctcta g gctgcctg    2160 actggaggcc ttccaagggg gtttcagtct ggacttatac agggaggcca g aagggctcc    2220 atgcactgga atgcggggac tctgcaggtg gattacccag gctcagggtt a acagctagc    2280 ctcctagttg agacacacct agagaagggt ttttgggagc tgaataaact c agtcacctg    2340 gtttcccatc tctaagcccc ttaacctgca gcttcgttta atgtagctct t gcatgggag    2400 tttctaggat gaaacactcc tccatgggat ttgaacatat gacttatttg t aggggaaga    2460 gtcctgaggg gcaacacaca agaaccaggt cccctcagcc cacagcactg t cttttttgct   2520 gatccacccc cctcttacct tttatcagga tgtggcctgt tggtccttct g ttgccatca    2580 cagagacaca ggcatttaaa tatttaactt atttatttaa caaagtagaa g ggaatccat    2640 tgctagcttt tctgtgttgg tgtctaatat ttgggtaggg tgggggatcc c caacaatca    2700 ggtcccctga gatagctggt cattgggctg atcattgcca gaatcttctt c tcctgggt     2760 ctggcccccc aaaatgccta acccaggacc ttggaaattc tactcatccc a aatgataat    2820 tccaaatgct gttacccaag gttagggtgt tgaaggaagg tagagggtgg g gcttcaggt    2880 ctcaacggct tccctaacca cccctcttct cttggcccag cctggttccc c ccacttcca    2940
```

-continued

```
ctcccctcta ctctctctag gactgggctg atgaaggcac tgcccaaaat t tcccctacc    3000 cccaactttc ccctacccccc aactttcccc accagctcca caaccctgtt t ggagctact   3060 gcaggaccag aagcacaaag tgcggtttcc caagcctttg tccatctcag c ccccagagt   3120 atatctgtgc ttggggaatc tcacacagaa actcaggagc acccctgcc t gagctaagg    3180 gaggtcttat ctctcagggg gggtttaagt gccgtttgca ataatgtcgt c ttatttatt   3240 tagcggggtg aatattttat actgtaagtg agcaatcaga gtataatgtt t atggtgaca   3300 aaattaaagg ctttcttata tgtttaaaaa aaaaaaaaaa aaaaaaaaaa a aaaaaaaa    3360 aaaaaaaara aaaaaaaaaa aaaaaaaaaa aaaaaataa aaaaaaaaa               3410
```

<210> SEQ ID NO 101
<211> LENGTH: 553
<212> TYPE: PRT
<213> ORGANISM: Homo sapien

<400> SEQUENCE: 101

```
Met Val Gln Arg Leu Trp Val Ser Arg Leu L eu Arg His Arg Lys Ala
  1               5                  10                  15

Gln Leu Leu Val Asn Leu Leu Thr Phe G ly Leu Glu Val Cys Leu
             20                  25                  30

Ala Ala Gly Ile Thr Tyr Val Pro Pro Leu L eu Leu Glu Val Gly Val
         35                  40                  45

Glu Glu Lys Phe Met Thr Met Val Leu Gly I le Gly Pro Val Leu Gly
     50                  55                  60

Leu Val Cys Val Pro Leu Leu Gly Ser Ala S er Asp His Trp Arg Gly
 65                  70                  75                  80

Arg Tyr Gly Arg Arg Arg Pro Phe Ile Trp A la Leu Ser Leu Gly Ile
                 85                  90                  95

Leu Leu Ser Leu Phe Leu Ile Pro Arg Ala G ly Trp Leu Ala Gly Leu
            100                 105                 110

Leu Cys Pro Asp Pro Arg Pro Leu Glu Leu A la Leu Leu Ile Leu Gly
        115                 120                 125

Val Gly Leu Leu Asp Phe Cys Gly Gln Val C ys Phe Thr Pro Leu Glu
    130                 135                 140

Ala Leu Leu Ser Asp Leu Phe Arg Asp Pro A sp His Cys Arg Gln Ala
145                 150                 155                 160

Tyr Ser Val Tyr Ala Phe Met Ile Ser Leu G ly Gly Cys Leu Gly Tyr
                165                 170                 175

Leu Leu Pro Ala Ile Asp Trp Asp Thr Ser A la Leu Ala Pro Tyr Leu
            180                 185                 190

Gly Thr Gln Glu Glu Cys Leu Phe Gly Leu L eu Thr Leu Ile Phe Leu
        195                 200                 205

Thr Cys Val Ala Ala Thr Leu Leu Val Ala G lu Glu Ala Ala Leu Gly
    210                 215                 220

Pro Thr Glu Pro Ala Glu Gly Leu Ser Ala P ro Ser Leu Ser Pro His
225                 230                 235                 240

Cys Cys Pro Cys Arg Ala Arg Leu Ala Phe A rg Asn Leu Gly Ala Leu
                245                 250                 255

Leu Pro Arg Leu His Gln Leu Cys Cys Arg M et Pro Arg Thr Leu Arg
            260                 265                 270

Arg Leu Phe Val Ala Glu Leu Cys Ser Trp M et Ala Leu Met Thr Phe
        275                 280                 285

Thr Leu Phe Tyr Thr Asp Phe Val Gly Glu G ly Leu Tyr Gln Gly Val
```

```
              290              295               300
Pro Arg Ala Glu Pro Gly Thr Glu Ala Arg A rg His Tyr Asp Glu Gly
305                 310              315                 320
Val Arg Met Gly Ser Leu Gly Leu Phe Leu G ln Cys Ala Ile Ser Leu
                325              330                 335
Val Phe Ser Leu Val Met Asp Arg Leu Val G ln Arg Phe Gly Thr Arg
                340              345                 350
Ala Val Tyr Leu Ala Ser Val Ala Ala Phe P ro Val Ala Ala Gly Ala
                355              360                 365
Thr Cys Leu Ser His Ser Val Ala Val T hr Ala Ser Ala Ala Leu
                370              375                 380
Thr Gly Phe Thr Phe Ser Ala Leu Gln Ile L eu Pro Tyr Thr Leu Ala
385                 390              395                 400
Ser Leu Tyr His Arg Glu Lys Gln Val Phe L eu Pro Lys Tyr Arg Gly
                405              410                 415
Asp Thr Gly Gly Ala Ser Ser Glu Asp Ser L eu Met Thr Ser Phe Leu
                420              425                 430
Pro Gly Pro Lys Pro Gly Ala Pro Phe Pro A sn Gly His Val Gly Ala
                435              440                 445
Gly Gly Ser Gly Leu Leu Pro Pro Pro A la Leu Cys Gly Ala Ser
450                 455                 460
Ala Cys Asp Val Ser Val Arg Val Val G ly Glu Pro Thr Glu Ala
465                 470              475                 480
Arg Val Val Pro Gly Arg Gly Ile Cys Leu A sp Leu Ala Ile Leu Asp
                485              490                 495
Ser Ala Phe Leu Leu Ser Gln Val Ala Pro S er Leu Phe Met Gly Ser
                500              505                 510
Ile Val Gln Leu Ser Gln Ser Val Thr Ala T yr Met Val Ser Ala Ala
                515              520                 525
Gly Leu Gly Leu Val Ala Ile Tyr Phe Ala T hr Gln Val Val Phe Asp
                530              535                 540
Lys Ser Asp Leu Ala Lys Tyr Ser Ala
545                 550

<210> SEQ ID NO 102
<211> LENGTH: 940
<212> TYPE: DNA
<213> ORGANISM: Human

<400> SEQUENCE: 102
tttactgctt ggcaaagtac cctgagcatc agcagagatg ccgagatgaa a tcagggaac     60 tcctagggga tgggtcttct attacctggg aacacctgag ccagatgcct t acaccacga    120 tgtgcatcaa ggaatgcctc cgcctctacg caccggtagt aaacatatcc c ggttactcg    180 acaaacccat cacctttcca gatggacgct ccttacctgc aggaataact g tgtttatca    240 atatttgggc tcttcaccac aaccctatt tctgggaaga ccctcaggtc t ttaaccct    300 tgagattctc cagggaaaat tctgaaaaaa tacatcccta tgccttcata c cattctcag    360 ctggattaag gaactgcatt gggcagcatt ttgccataat tgagtgtaaa g tggcagtgg    420 cattaactct gctccgcttc aagctggctc cagaccactc aaggcctccc c agcctgttc    480 gtcaagttgt cctcaagtcc aagaatggaa tccatgtgtt tgcaaaaaaa g tttgctaat    540 tttaagtcct ttcgtataag aattaatgag acaattttcc taccaaggaa g aacaaaag    600 gataaatata atacaaaata tatgtatatg gttgtttgac aaattatata a cttaggata   660
```

```
cttctgactg gttttgacat ccattaacag taatttaat ttctttgctg t atctggtga       720 aacccacaaa aacmcctgaa aaactcaag ctgacttcca ctgcgaaggg a aattattgg       780 tttgtgtaac tagtggtaga gtggctttca agcatagttt gatcaaaact c cactcagta     840 tctgcattac ttttatytyt gcaaatatct gcatgatagc tttattytca g ttatctttc    900 cccataataa aaaatatctg ccaaaaaaaa aaaaaaaaa                              940
```

<210> SEQ ID NO 103
<211> LENGTH: 529
<212> TYPE: DNA
<213> ORGANISM: Human

<400> SEQUENCE: 103

```
tttttttttt ttttactga tagatggaat ttattaagct tttcacatgt g atagcacat     60 agttttaatt gcatccaaag tactaacaaa aactctagca atcaaraatg g cagcatgtt   120 attttataac aatcaacacc tgtggctttt aaaatttggt tttcataara t aatttatac   180 tgaagtaaat ctagccatgc ttttaaaaaa tgctttaggt cactccaagc t tggcagtta  240 acatttggca taaacaataa taaaacaatc acaatttaat aaataacaaa t acaacattg  300 taggccataa tcatatacag tataaggaaa aggkggtagt gttgagtaag c agttattag  360 aatagaatac cttggcctct atgcaaatat gtctaracac tttgattcac t cagccctga   420 cattcagttt tcaaagtagg agacaggttc tacagtatca ttttacagtt t ccaacacat   480 tgaaaacaag tagaaaatga tgagttgatt tttattaatg cattacatc                 529
```

<210> SEQ ID NO 104
<211> LENGTH: 469
<212> TYPE: DNA
<213> ORGANISM: Human

<400> SEQUENCE: 104

```
cccaacacaa tggataaaaa cacttatagt aaatggggac attcactata a tgatctaag     60 aagctacaga ttgtcatagt tgtttttcctg ctttacaaaa ttgctccaga t ctggaatgc  120 cagtttgacc tttgtcttct ataatatttc ctttttttcc cctctttgaa t ctctgtata   180 tttgattctt aactaaaatt gttctcttaa atattctgaa tcctggtaat t aaaagtttg   240 ggtgtatttt ctttacctcc aaggaaagaa ctactagcta caaaaaatat t ttggaataa   300 gcattgtttt ggtataaggt acatattttg gttgaagaca ccagactgaa g taaacagct  360 gtgcatccaa tttattatag ttttgtaagt aacaatatgt aatcaaactt c taggtgact   420 tgagagtgga acctcctata tcattattta gcaccgtttg tgacagtaa                 469
```

<210> SEQ ID NO 105
<211> LENGTH: 744
<212> TYPE: DNA
<213> ORGANISM: Human

<400> SEQUENCE: 105

```
ggcctgggac aggattgagg tatgttgcag cctccagggc ctgggtctc c tgcatgaag       60 aatacccctc cccatttgac tgtgaacttt tggcctgga ttctggagaa c agatttcca  120 ggattgtcag ccagaaggca gacagatgca ggcacctacc aagcctgac c tcaggaagt    180 ggccctgccc tacagcccag ttgctcagcc agggctgaag gccatgggc c ccagcaccc   240 ttgcttcagt gccagcccct ggaaggaacc tcacaacagg gatacagcaa g gacactcca  300
```

-continued

```
gttcccccag tcctgccatg gtgctaccct gagggacagg gatggagaca g ggcagccag      360 gtttgccagg acctgcatag cgggcccaag actgcccttc ctcttaagtc a tgccaaagc      420 ctccctgccc agtctgagac agtcgctggc aggtgaccac gacctgcgtg g ccctcccgg      480 cagttgtcat ggtggttgta ccccacccca tccccctgag agacatggg c tcagtccca       540 tgcctggtgc ccacagccac aaagatggcc atgggtctct agcctgatat t cgtggcctg      600 gcagggtca gcaccctga gggcatccaa gccatggtca gaggaaagtg t tggcaggct        660 cggcacagcc aaagaagtca ggacccacga gacggggaa gccttccaga g ccttcacct       720 tcacagggtc aaacttccag taga                                              744

<210> SEQ ID NO 106
<211> LENGTH: 401
<212> TYPE: DNA
<213> ORGANISM: Human

<400> SEQUENCE: 106
acattgttag gtgctgacct agacagagat gaactgaggt ccttgttttg t tttgttcat      60 aatacaaagg tgctaattaa tagtatttca gatacttgaa gaatgttgat g gtgctagaa     120 gaatttgaga agaaatactc ctgtattgag ttgtatcgtg tggtgtattt t ttaaaaaat     180 ttgatttagc attcatattt tccatcttat tcccaattaa agtatgcag a ttatttgcc      240 caaatcttct tcagattcag catttgttct ttgccagtct cattttcatc t tcttccatg     300 gttccacaga agctttgttt cttgggcaag cagaaaaatt aaattgtacc t attttgtat    360 atgtgagatg tttaaataaa ttgtgaaaaa aatgaaataa a                          401

<210> SEQ ID NO 107
<211> LENGTH: 1009
<212> TYPE: DNA
<213> ORGANISM: Human

<400> SEQUENCE: 107
cgagctatta tggtacggaa ctttttttaa tgaggaattt catgatgatt t aggaatttt      60 ctctcttgga aaaggcttcc cctgtgatga aaatgatgtg ccagctaaaa t tgtgtgcca    120 tttaaaaact gaaatatttt taaaattatt tgtctatatt ctaaattgag c tttggatca    180 aactttaggc caggaccagc tcatgcgttc tcattcttcc tttctcact c tttctctca     240 tcactcacct ctgtattcat tctgttgttt gggatagaaa atcataaag a gccaaccca     300 tctcagaacg ttgtggattg agagagacac tacatgactc caagtatatg a gaaaggac     360 agagctctaa ttgataactc tgtagttcaa aggaaaaga gtatgcccaa t tctctctac     420 atgacatatt gagatttttt ttaatcaact tttaagatag tgatgttctg t tctaaactg    480 ttctgttttta gtgaaggtag attttttataa aacaagcatg gggattcttt t ctaaggtaa    540 tattaatgag aagggaaaaa agtatcttta acagctcttt gttgaagcct g tggtagcmc    600 attatgttta taattgcaca tgtgcacata atctattatg atccaatgca a atacagctc     660 caaaatatatt aaatgtatat atattttaaa atgcctgagg aaatacattt t tcttaataa    720 actgaagagt ctcagtatgg ctattaaaat aattattagc ctcctgttgt g tggctgcaa    780 aacatcacaa agtgaccggt cttgagacct gtgaactgct gccctgttta g taaataaaa    840
```

```
ttaatgcatt tctagagggg gaatatctgc catccagtgg tggaaatgtg g agtaaagaa      900 gctggtggtc tgcttctgtg ctgtatgcca gccttttgcc ttaagttgag a ggaggtcaa      960 ctttagctac tgtctttggt ttgagagcca tggcaaaaaa aaaaaaaaa                  1009
```